(12) United States Patent
Griffiths et al.

(10) Patent No.: US 7,230,085 B2
(45) Date of Patent: Jun. 12, 2007

(54) ANTI-DOTA ANTIBODY

(75) Inventors: Gary L. Griffiths, Morristown, NJ (US); Hans J. Hansen, Picayune, MS (US); Serengulam V. Govindan, Summit, NJ (US); Michelle Losman, South Orange, NJ (US); Zhengxing Qu, Warren, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 162 days.

(21) Appl. No.: 10/305,268

(22) Filed: Nov. 27, 2002

(65) Prior Publication Data

US 2003/0124057 A1    Jul. 3, 2003

Related U.S. Application Data

(60) Provisional application No. 60/333,479, filed on Nov. 28, 2001.

(51) Int. Cl.
*C12P 21/08* (2006.01)
*C07K 16/44* (2006.01)
*G01N 33/534* (2006.01)
*A61K 51/10* (2006.01)

(52) U.S. Cl. ............... 530/387.3; 530/388.1; 530/388.9; 530/391.3; 530/304; 436/548

(58) Field of Classification Search ............ 530/387.1, 530/300; 435/810
See application file for complete search history.

(56) References Cited

U.S. PATENT DOCUMENTS

| | | | |
|---|---|---|---|
| 5,256,395 A | 10/1993 | Barbet et al. | |
| 5,274,076 A | 12/1993 | Barbet et al. | |
| 5,633,425 A | 5/1997 | Lonberg et al. | |
| 5,663,301 A * | 9/1997 | Johnson | 530/363 |
| 5,811,267 A | 9/1998 | Ring | |
| 5,827,690 A | 10/1998 | Meade et al. | |
| 5,973,116 A | 10/1999 | Epenetos et al. | |
| 6,458,933 B1 | 10/2002 | Hansen | |
| 2002/0076406 A1 | 6/2002 | Leung | |

FOREIGN PATENT DOCUMENTS

EP   0 369 567 A   5/1990

OTHER PUBLICATIONS

Stryer et al, in Biochemistry, Third edition, W H Freeman Company, New York, pp. 31-33, 1998.*
Attwood et al, The Babel of Bioinformatics, 2000, Science vol. 290 No. 5491: 471-473.*
Kuby et al, Immunology, Second edition, pp. 86-96, 1994.*
Castel et al, J Histochem Cytochem 26(7): 581-592, Jul. 1978.*
Denardo et al., "Antibody phage libraries for the next generation of tumor targeting radioimmunotherapeutics," *Clinical Cancer Research*, Oct. 1999, pp. 3213s-3218s, vol. 5, No. 10 Suppl.

Perico et al., "The humoral immune response to macrocyclic chelating agent DOTA depends on the carrier molecule," *Journal of Nuclear Medicine*, Nov. 2001, pp. 1697-1703, vol. 42, No. 11, Society of Nuclear Medicine, U.S.A.
Govindan et al., "Advances in the use of monoclonal antibodies in cancer radiotherapy," *Pharmaceutical Science & Technology Today*, Mar. 2000, pp. 90-98, vol. 3, No. 3.
Govindan et al., "Yttrium-labeled complementarity-determining-region-grafted monoclonal antibodies for radioimmunotherapy: Radiolabeling and animal biodistribution studies," *Bioconjugate Chemistry*, Nov. 1998, pp. 773-782, vol. 9, No. 6.
Barbas III et al., "Combinatorial Immunoglobulin Libraries on the Surface of Phage (Phabs): Rapid Selection of Antigen-Specific Fabs," *Methods: A Comparison to Methods in Enzymology*, Apr. 1991, pp. 119-124, vol. 2, No. 2.
Barbet et al., "Radioimmunodetection of Medullary Thyroid Carcinoma Using Indium-111 Bivalent Hapten and Anti-CEA X Anti-DTPA-Indium Bispecific Antibody," *The Journal of Nuclear Medicine*, Jul. 1998, pp. 1172-1178, vol. 39, No. 7.
Bardiès et al., "Bispecific Antibody and Iodine-131-Labeled Bivalent Hapten Dosimetry in Patients with Medullary Thyroid or Small-Cell Lung Cancer," *The Journal of Nuclear Medicine*, Nov. 1996, pp. 1853-1859, vol. 37, No. 11.
Baxter et al., "Pharmacokinetic Analysis of the Perivascular Distribution of Bifunctional Antibodies and Haptens: Comparison with Experimental Data," *Cancer Research*, Oct. 15, 1992, pp. 5838-5844, vol. 52, No. 20.
Bei et al., "Baculovirus expression of a functional single-chain immunoglobulin and its IL-2 fusion protein," *Journal of Imunological Methods*, 1995, pp. 245-255, vol. 186.
Boden et al., "Preliminary Study of the Metal Binding Site of an Anti-DTPA-Indium Antibody by Equilibrium Binding Immunoassays and Immobilized Metal Ion Affinity Chromatography," *Bioconjugate Chem.*, 1995, pp. 373-379, vol. 6.
Boerman et al., "Pretargeting of Renal Cell Carcinoma: Improved Tumor Targeting with a Bivalent Chelate," *Cancer Research*, Sep. 1, 1999, pp. 4400-4405, vol. 59.
Bosslet et al., "Generation of bispecific monoclonal antibodies for two phase radioimmunotherapy," *Br. J. Cancer*, 1991, pp. 681-686, vol. 63.
Carter et al., "Humanization of an anti-p185[HER2] antibody for human cancer therapy," *Proc. Natl. Acad. Sci. USA*, May 1992, pp. 4285-4289, vol. 89.
Casey et al., "Clearance of yttrium-90-labelled anti-tumour antibodies with antibodies raised against the 12N4 DOTA macrocycle," *Br. J. Cancer*, 1998, pp. 1307-1312, vol. 78, No. 10.
Chatal et al., "Bifunctional Antibodies for Radioimmunotherapy," *Hybridoma*, 1995, pp. 125-128, vol. 14, No. 2.

(Continued)

*Primary Examiner*—Christina Chan
*Assistant Examiner*—Phuong Huynh
(74) *Attorney, Agent, or Firm*—Faegre & Benson LLP

(57) ABSTRACT

The present invention relates to an antibody or antibody fragment that binds to 1,4,7,10-tetrazacyclododecane-N,N', N",N"'-tetraacetic acid (DOTA), which is bound to an alkylamino group through one of its pendant carb.oxyl groups.

6 Claims, 4 Drawing Sheets

OTHER PUBLICATIONS

Colman, "Production of therapeutic proteins in the milk of transgenic livestock," *Biochem. Soc. Symp.*, 1996, pp. 141-147, No. 63, Great Britain.

Coloma et al., "Design and production of novel tetravalent bispecific antibodies," *Nature Biotechnology*, Feb. 1997, pp. 159-163, vol. 15.

De Stasio et al., "Gadolinium in Human Glioblastoma Cells for Gadolinium Neutron Capture Therapy," *Cancer Research*, May 15, 2001, pp. 4272-4277, vol. 61.

Denardo et al., "Phage Library-derived Human Anti-TETA and Anti-DOTA ScFv for Pretargeting RIT," *Hybridoma*, 1999, pp. 13-21, vol. 18, No. 1.

Doiron et al., "Fluorsecence Bronchoscopy for Detection of Lung Cancer," *Chest*, Jul. 1979, pp. 27-32, vol. 76, No. 1.

Feng et al., "New Anti-Cu-TETA and Anti-Y-DOTA Monoclonal Antibodies for Potential Use in the Pre-Targeted Delivery of Radiopharmaceuticals to Tumor," *Hybridoma*, 1998, pp. 125-132, vol. 17, No. 2.

Fiedler et al., "High-Level Production and Long-Term Storage of Engineered Antibodies in Transgenic Tobacco Seeds," *Bio/Technology*, Oct. 1995, pp. 1090-1093, vol. 13.

Fiedler et al., "Optimization of scFv antibody production in transgenic plants," *Immunotechnology*, 1997, pp. 205-216, vol. 3.

Fitzgerald et al., "Improved tumour targeting by disulphide stabilized diabodies expressed in *Pichia pastoris,*" *Protein Engineering*, 1997, pp. 1221-1225, vol. 10, No. 10.

Gautherot et al., "Therapy for Colon Carcinoma Xenografts with Bispecific Antibody-Targeted, Iodine-131-Labeled Bivalent Hapten," *Cancer, Supplement, Sixth Conference on Radioimmunodetection and Radioimmunotherapy of Cancer*, Oct. 10-12, 1996, pp. 2618-2623.

Goodwin et al., "Pharmacokinetics of Pretargeted Monoclonal Antibody 2D12.5 and $^{88}$Y-Janus-2-($p$-Nitrobenzyl)-1,4,7,10-tetraazacyclododecanetetraacetic Acid (DOTA) in BALB/c Mice with KHJJ ouse Adenocarcinoma: A Model for $^{90}$Y Radioimmunotherapy[1,2]," *Cancer Research*, Nov. 15, 1994, pp. 5937-5946, vol. 54, No. 22.

Goodwin et al., "Pre-Targeted Immunoscintigraphy of Murine Tumors with Indium-111-Labeled Bifunctional Haptens," *The Journal of Nuclear Medicine*, Feb. 1988, pp. 226-234, vol. 29, No. 2.

Goodwin et al., "Pretargeted Immunoscintigraphy: Effect of Hapten Valency on Murine Tumor Uptake," *The Journal of Nuclear Medicine*, Nov. 1992, pp. 2006-2013, vol. 33, No. 11.

Hosono et al., "Biodistribution and Dosimetric Study in Medullary Thyroid Cancer Xenograft Using Bispecific Antibody and Iodine-125-Labeled Bivalent Hapten," *The Journal of Nuclear Medicine*, Sep. 1998, pp. 1608-1613, vol. 39, No. 9.

Hosono et al., "Two-Step Targeting and Dosimetry for Small Cell Lung Cancer Xenograft with Anti-NCAM/Antiistamine Bispecific Antibody and Radioiodinated Bivalent Hapten," *The Journal of Nuclear Medicine*, Jul. 1999, pp. 1216-1221, vol. 40, No. 7.

Jackson et al., "Antigen specificity and tumour targeting efficiency of a human carcinoembryonic antigen-specific scFv and affinity-matured derivatives," *British Journal of Cancer*, pp. 181-188, vol. 78, No. 2.

Janevik-Ivanovska et al., "Bivalent Hapten-Bearing Peptides Designed for Iodine-131 Pretargeted Radioimmunotherapy," *Bioconjugate Chem.*, 1997, pp. 526-533, vol. 8.

Jones et al., "Replacing the complementarity-determining regions in a human antibody with those from a mouse," *Nature*, May 29, 1986, pp. 522-525, vol. 321.

Karacay et al., "Experimental Pretargeting Studies of Cancer with a Humanized anti-CEA x Murine anti-[In-DTPA] Bispecific Antibody Construct and a $^{99m}$Tc-/$^{188}$Re-Labeled Peptide," *Bioconjugate Chem.*, 2000, pp. 842-854, vol. 11.

Kraeber-Bodéré et al., "Bispecific Antibody and Bivalent Hapten Radioimmunotherapy in CEA-Producing Medullary Thyroid Cancer Xenograft," *The Journal of Nuclear Medicine*, Jan. 1999, pp. 198-204, vol. 40, No. 1.

Kraeber-Bodéré et al., "Radioimmunotherapy in Medullary Throid Cancer Using Bispecific Antibody and Iodine 131-labeled Bivalent Hapten: Preliminary Results of a Phase I/II Clinical Trial," *Clinical Cancer Research*, Oct. 1999 (Suppl.), pp. 3190s-3198s, vol. 5.

Kraeber-Bodéré et al., "Toxicity and Efficacy of Radioimmunotherapy in Carcinoembryonic Antigen-producing Medullary Thyroid Cancer Xenograft: Comparison of Iodine 131-labeled F(ab')$_2$ and Pretargeted Bivalent Hapten and Evaluation of Repeated Injections," *Clinical Cancer Research*, Oct. 1999 (Suppl.), pp. 3183s-3189s, vol. 5.

Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," *The Journal of Nuclear Medicine*, Oct. 1993, pp. 1662-1671, vol. 34, No. 10.

Le Doussal et al., "In Vitro and In Vivo Targeting of Radiolabeled Monovalent and Divalent Haptens with Dual Specificity Monoclonal Antibody Conjugates: Enhanced Divalent Hapten Affinity for Cell-Bound Antibody Conjugate," *The Journal of Nuclear Medicine*, Aug. 1989, pp. 1358-1366, vol. 30, No. 8.

Le Doussal et al., "Targeting of Indium 111-labeled Bivalent Hapten to Human Melanoma Mediated by Bispecific Monoclonal Antibody Conjugates: Imaging of Tumors Hosted in Nude Mice," *Cancer Research*, Jun. 1, 1990, pp. 3445-3452, vol. 50.

Mack et al., "A small bispecific antibody construct expressed as a functional single-chin molecule with high tumor cell cytotoxicity," *Proc. Natl. Acad. Sci. USA*, Jul. 1995, pp. 7021-7025, vol. 92.

Mahiouz et al., "Expression of recombinant anti-E-selectin single-chain Fv antibody fragments in stably transfected insect cell lines," *Journal of Immunological Methods*, 1998, pp. 149-160, vol. 212.

Meares et al., "Conjugation of Antibodies with Bifunctional Chelating Agents: Isothiocyanate and Bromoacetamide Reagents, Methods of Analysis, and Subsequent Addition of Metal Ions," *Analytical Biochemistry*, Oct. 1984, pp. 68-78, vol. 142, No. 1.

Mendez et al., "Functional transplant of megabase human immunoglobulin loci recapitulates human antibody response in mice," *Nature Genetics*, Feb. 1997, pp. 146-156, vol. 15, No. 2.

Miller, "Baculoviruses As Gene Expression Vectors," *Ann. Rev. Microbiol.*, 1988, pp. 177-199, vol. 42.

Orlandi et al., "Cloning immunoglobulin variable domains for expression by the polymerase chain reaction," *Proc. Natl. Acad. Sci. USA*, May 1989, pp. 3833-3837, vol. 6.

Osbourn et al., "Generation of a panel of related human scFv antibodies with high affinities for human CEA," *Immunotechnology*, 1996, pp. 181-196, vol. 2.

Peltier et al., "Radioimmunodetection of Medullary Thyroid Cancer Using a Bispecific Anti-CEA/Anti-Indium-DTPA Antibody and an Indium-111-Labeled DTPA Dimer," *The Journal of Nuclear Medicine*, Aug. 1993, pp. 1267-1273, vol. 34, No. 8.

Ridder et al., "Generation of Rabbit Monoclonal Antibody Fragments from a Combinatorial Phage Display Library and Their Production in the Yeast *Pichia pastoris,*" *Bio/Technology*, Mar. 1995, pp. 255-260, vol. 13.

Riechmann et al., "Reshaping human antibodies for therapy," *Nature*, Mar. 24, 1988, pp. 323-327, vol. 332.

Rouvier et al., "Targeting Medullary Thyroid Carcinomas with Bispecific Antibodies and Bivalent Haptens," *Horm. Res.*, 1997, pp. 163-167, vol. 47.

Sambrook et al., "Molecular Cloning, A Laboratory Manual, Second Edition," (Table of Contents Only).

Singer et al., "Optimal Humanization of 1B4, an Anti-CD18 Murine Monoclonal Antibody, Is Achieved by Correct Choice of Human V-Region Framework Sequences," *The Journal of Immunology*, Apr. 1, 1993, pp. 2844-2857, vol. 150, No. 7, USA.

Stickney et al., "Bifunctional Antibody: A Binary Radiopharmaceutical Delivery System for Imaging Colorectal Carcinoma," *Cancer Research*, Dec. 15, 1991, pp. 6650-6655, vol. 51, No. 24.

*The Journal of Circulation, Respiration and Related Systems*, Jul.-Dec. 1979, vol. 76, (Author Index Only).

Tomizuka et al., "Functional expression and germline transmission of a human chromosome fragment in chimaeric mice," *Nature Genetics*, Jun. 1997, pp. 133-143, vol. 16, No. 1.

Vaughan et al., "Human Antibodies with Sub-nanomolar Affinites Isolated from a Large Non-immunized Phage Display Library," *Nature Biotechnology*, Mar. 1996, pp. 309-314, vol. 14, No. 3.

Verhoeyen et al., "Reshaping human antibodies: Grafting an Antilsozyme Activity," *Science*, Mar. 25, 1988, pp. 1534-1536, vol. 239.

Vuillez et al., "Radioimmunotherapy of Small Cell Lung Carcinoma with the Two-Step Method using a Bespecific Anti-Carcinoembryonic Antigen/Anti-Diethylenetriaminepentaacetic Acid (DTPA) Antibody and Iodine-131 Di-DTPA Hapten: Results of a Phase I/II Trial," *Clinical Cancer Research*, Oct. 1999 (Suppl), pp. 3259s-3267s, vol. 5.

Vuillez et al., "Two-Step Immunoscintigraphy for Non-Small-Cell Lung Cancer Staging Using a Bispecific Anti-CEA/Anti-Indium-DTPA Antibody and an Indium-111-Labeled DTPA Dimer," *The Journal of Nuclear Medicine*, Apr. 1997, pp. 507-511, vol. 38, No. 4.

Winter et al., "Making Antibodies by Phage Display Technology," *Annu. Rev. Immunol.*, 1994, pp. 433-455, vol. 12, © Annual Reviews, Inc.

Yang et al., "One Hundred Seventy-Fold Increase in Excretion of an FV Fragment-Tumor Necrosis Factor Alpha Fusion Protein (sFV/TNF-α) from *Escherichia coli* Caused by the Sunergistic Effects of Glycine and Triton X-100," *Applied and Environmental Microbiology*, Aug. 1998, pp. 2869-2874, vol. 64, No. 8.

Zhu et al., "High Level Secretion of a Humanized Bispecific Diabody from *Escherichia coli*," *Bio/Technology*, Feb. 1996, pp. 192-196, vol. 14.

Zhu et al., "Tumor Pretargeting for Radioimmunodetection and Radioimmunotherapy," *The Journal of Nucleard Medicine*, Jan. 1998, pp. 65-76, vol. 39, No. 1.

* cited by examiner

Figure 3

```
GAAGTGATGCTCTGGTGAGTCTGGGGGGCTTAGTGAAACCTGGAGGGTCCCTGACACTCTCCTGTGCAGCCTCTGGATTCACTTTTACT       90
 E  V  M  L  V  E  S  G  G  G  L  V  K  P  G  G  S  L  T  L  S  C  A  A  S  G  F  T  F  T     30

GCCCATGCCATGTCTTGGGTCCGCCAGACTCCGGAGAGAGGCTGGAGTGGGTCGCAACCATTAGTGGTGGTACTTACACCTACTTT      180
 A  H  A  M  S  W  V  R  Q  T  P  E  K  R  L  E  W  V  A  T  I  S  G  G  T  Y  T  Y  F       60
 ‾‾‾‾‾‾‾‾‾‾‾                                                ‾‾‾‾‾‾‾‾‾‾‾‾‾‾‾‾‾‾‾‾‾‾‾‾‾‾‾‾‾
    CDR1                                                                 CDR2

CCAGACAGTTTTCAGGGCCGATTCACCATCTCCAGCGACAATGCCAAGAACACCCTGTATTTACAAATGAGCAGTCTGAGGTCTGAGGAC   270
 P  D  S  F  Q  G  R  F  T  I  S  S  D  N  A  K  N  T  L  Y  L  Q  M  S  S  L  R  S  E  D     90
 ‾‾‾‾‾‾‾‾‾‾‾‾‾‾‾

ACGTCCATGTATTTCTGTACAAGACATGGAGACTATAGGTACGCCCTTTGTTACTGGGGCCAAGGGACTCTGGTCACTGTCTCTGCA      354
 T  S  M  Y  F  C  T  R  H  G  D  Y  R  Y  A  F  G  Y  W  G  Q  G  T  L  V  T  V  S  A       119
                         ‾‾‾‾‾‾‾‾‾‾‾‾‾‾‾‾‾‾‾‾‾‾‾‾‾‾‾‾‾‾‾‾
                                         CDR3
```

Figure 4

```
GTTGTGACTCAGGAATCTGCACTCACCACATCACCTGTGAAACAGTCACACTCACTTGTCGCTCAAGTAGTGGGGCTGTTACAACTAAT    90
 V  V  T  Q  E  S  A  L  T  T  S  P  G  E  T  V  T  L  T  C  R  S  S  S  G  A  V  T  T  N    30
                                                                  ────────────────────────
                                                                            CDR1

AATTATGCCAACTGGGTCCAAGAAAAACCAGATCATTTATTCACTGGTCTAATAGGTGGTACCAACAACCGAGCTCCAGGTGTTCCTGCC   180
 N  Y  A  N  W  V  Q  E  K  P  D  H  L  F  T  G  L  I  G  G  T  N  N  R  A  P  G  V  P  A    60
 ─────────                                                     ───────────────────
                                                                       CDR2

AGATTCTCAGGCTCCCTGATTGGAGACAAGGCTGCCCTCACCATCACAGGGCACAGACTGAGGATGAGGCAATATATTTCTGTGCTCTA   270
 R  F  S  G  S  L  I  G  D  K  A  A  L  T  I  T  G  A  Q  T  E  D  E  A  I  Y  F  C  A  L    90

TGGTTCAGCGACCACTGGGTGTTCGGTGGAGGAACCGAACTGACTGTCCTAGGC                                       324
 W  F  S  D  H  W  V  F  G  G  G  T  E  L  T  V  L  G                                        108
 ────────────────
       CDR3
```

ANTI-DOTA ANTIBODY

CROSS-REFERENCE TO RELATED APPLICATIONS

This application claims priority from U.S. Provisional Ser. No. 60/333,479, filed Nov. 28, 2001, which is incorporated herein in its entirety.

BACKGROUND OF THE INVENTION

1. Field of the Invention

The present invention relates to an antibody or antibody fragment that binds to 1,4,7,10-tetrazacyclododecane-N,N', N'',N'''-tetraacetic acid (DOTA),which is bound to an alkylamino group through one of its pendant carboxyl groups.

2. Related Art

Multi-specific antibodies (msAbs) offer the possibility of improved efficacy in the delivery of radionuclides using antibody targeting. Radionuclide therapy can be more efficacious when the radionuclide is attached to a moiety that is bivalent toward the pretargeted msAb. For example, crosslinking of pretargeted msAb localized at the disease target was effected by a bivalent hapten moiety that carried the radiolabel (Barbet, U.S. Pat. No. 5,256,395). This approach was used for radioimmunotherapy (RAIT) using the radionuclide iodine-131, which had been attached to a suitable bivalent hapten. The recognition system of the second arm of the msAb used in these studies was based on an indium complex of the chelate diethylenetriaminepentaacetic acid (DTPA), which had been doubly attached to a peptide [tyrosyl-lysine], which could be radioiodinated at its tyrosine residue. Ironically, the DTPA-Tyr.Lys(DTPA).OH, although based on and containing chelating agents, was not useful for any radiometals other than indium, since the action of metal binding by metals other than indium effectively destroyed the affinity of the di-DTPA peptide for the recognizing arm of the msAb. To overcome this deficiency, other series of antibodies were raised that did not depend on recognition of a metal complex (Barbet, U.S. Pat. No. 5,274,076). While the reagents made were designed to be hydrophilic in nature, it was mandatory that a chelating agent would also need to be appended to the recognition unit, via a backbone structure of some kind, and this certainly further complicated preparative procedures. In addition, each increase in size of the bivalent hapten could result in a poorer, incomplete clearance pattern in vivo, destroying one of the major advantages of the system based on the DTPA-Tyr.Lys(DTPA).OH recognition peptide.

Known antibodies directed towards other chelating agents are not versatile in recognizing different metal-chelator complexes, nor do they possess high binding affinities to any metal-chelator complex. Antibodies to yttrium-DOTA have been previously prepared using a 2-benzyl-DOTA (a ring-carbon derivatized chelating agent) derivative linked to keyhole limpet hemocyanin (KLH) as immunogen. Several mAbs were described, all of which were $IgG_1$ heavy chain and kappa light chain, with the exception of one that was $IgG_3$ heavy chain and lambda light chain. These anti-DOTA antibodies all had a relatively low affinity ($\cong 2\times10^{-8}$M), which may not be optimal for use in a pretargeting approach. The mAb selected as best for further study ($IgG_1$ and kappa) was found to bind equally well to both Gd-DOTA and to Y-DOTA, but much less well to other metal complexes such as In-DOTA, Cu-DOTA and Fe-DOTA. The authors ascribed this to the fact that the Y- and Gd-complexes were 9-coordinate [including one water molecule] whereas complexes with In-, Fe- and Cu- were 8-7- and 6-coordinate, respectively. The best binding metals were thought to be best due to the fact that the DOTA ring immunogen has all four amino and all four carboxyl groups available for metal binding, resulting in a higher denticity complex. Metals forming complexes with DOTA of lower denticity did not bind as well to the anti-DOTA-yttrium mAb.

Tissue specificity can be provided by monoclonal antibodies and peptides that target disease-associated antigens and receptors, respectively. However, direct binding of nuclides to these targeting agents often results in agents that have poor biodistribution characteristics, and therefore poor imaging and therapy qualities.

Thus a continuing need exists for a universal antibody directed towards a variety of chelator-metal complexes. The universal antibody will allow the skilled artisan the flexibility of using a single antibody for recognizing and maximizing uptakes of diagnostic and therapeutic nuclides and radionuclides, specifically in high amounts at diseased tissue, compared to surrounding normal tissues. Maximization of radioactivity in this manner can be expected to drastically improve imaging quality during diagnostic techniques and therapeutic ratios during therapy procedures.

SUMMARY OF THE INVENTION

The present invention relates to an antibody or antibody fragment that binds to 1,4,7,10-tetrazacyclododecane-N,N', N'',N'''-tetraacetic acid (DOTA),which is bound to an alkylamino group through one of its pendant carboxyl groups, or a metal complex thereof.

The invention further relates to an antibody reactive with an epitope comprised of the macrocyclic ring 1,4,7,10,-tetraazacyclododecane-N,N,N,N-tetraacetic acid (DOTA), or a metal complex thereof, an aminoalkyl moiety, and about one to seven amino acids (AAs), bound to said aminoalkyl moiety.

BRIEF DESCRIPTION OF THE DRAWINGS

FIG. 3 depicts the DNA (SEQ ID NO: 1) and amino acid (SEQ ID NO: 2) sequences of LG1VH. Amino acid sequence is shown as one-letter codes. The amino acid residues form CDRs (according to Kabat numbering scheme) are underlined and indicated as H1-3.

FIG. 4 depicts the DNA (SEQ ID NO: 3) and amino acid (SEQ ID NO: 4) sequences of LG1VL. Amino acid sequence is shown as one-letter codes. The amino acid residues form CDRs (according to Kabat numbering scheme) are underlined and indicated as L1-3.

DETAILED DESCRIPTION OF THE INVENTION

The present invention relates to an antibody or antibody fragment that binds to 1,4,7,10-tetrazacyclododecane-N,N', N",N"'-tetraacetic acid (DOTA),which is bound to an alkyl-amino group through one of its pendant carboxyl groups. Moreover, the invention relates to a metal complex of DOTA wherein the metal bound to DOTA binds with essentially equivalent affinity to peptide-DOTA-metal complexes of gallium, indium, gadolinium, yttrium, lutetium, and lead.

The present invention further relates to an antibody or antibody fragment that binds to 1,4,7,10-tetrazacyclodode-cane-N,N',N",N"'-tetraacetic acid (DOTA),which is bound to an alkyl-amino group through one of its pendant carboxyl groups, or a metal complex thereof, and preferably wherein the antibody or antibody fragment binds to DOTA with essentially equivalent affinity as it binds to peptide-DOTA-metal complexes of gallium, indium, gadolinium, yttrium, lutetium, and lead. In another preferred embodiment, the binding affinity of the antibody or antibody fragment for various metal complexes is within 100-fold, more or less, more preferably within 10-fold, more or less, of each other, relative to the yttrium complex to which the LG-1 antibody was originally raised. For example, if the affinity of the LG-1 antibody for yttrium-DOTA is 1 nanomolar, the "essentially equivalent affinity to peptide-DOTA-metal complexes of gallium, indium, gadolinium, yttium, lutetium and lead" is between 0.01 nanomolar and 100 nanomolar; preferably, between 0.1 nanomolar and 10 nanomolar.

The immunogen used for the preparation of anti-DOTA mAb is made in a very specific manner. The carrier protein used to bear the DOTA hapten is itself a monoclonal antibody termed hLL2 (complementarity-determining region-grafted, or humanized, LL2; anti-CD22), as distinct from many immunogens used in the generation of antibodies, which are often poorly defined in structure. Being humanized, this immunogen represents a highly pure, yet distinctly foreign protein to the rodent. In addition, the linkage of the DOTA chelate to the hLL2 carrier protein is performed with a 'minimal linkage' type of strategy, in that only one of the endogenous carboxyl groups of the DOTA macrocycle is activated using an in situ active ester method to effect direct coupling to hLL2 lysine groups. In this manner there is no possibility of generating antibodies to any extra linking moiety.

Figure 1:
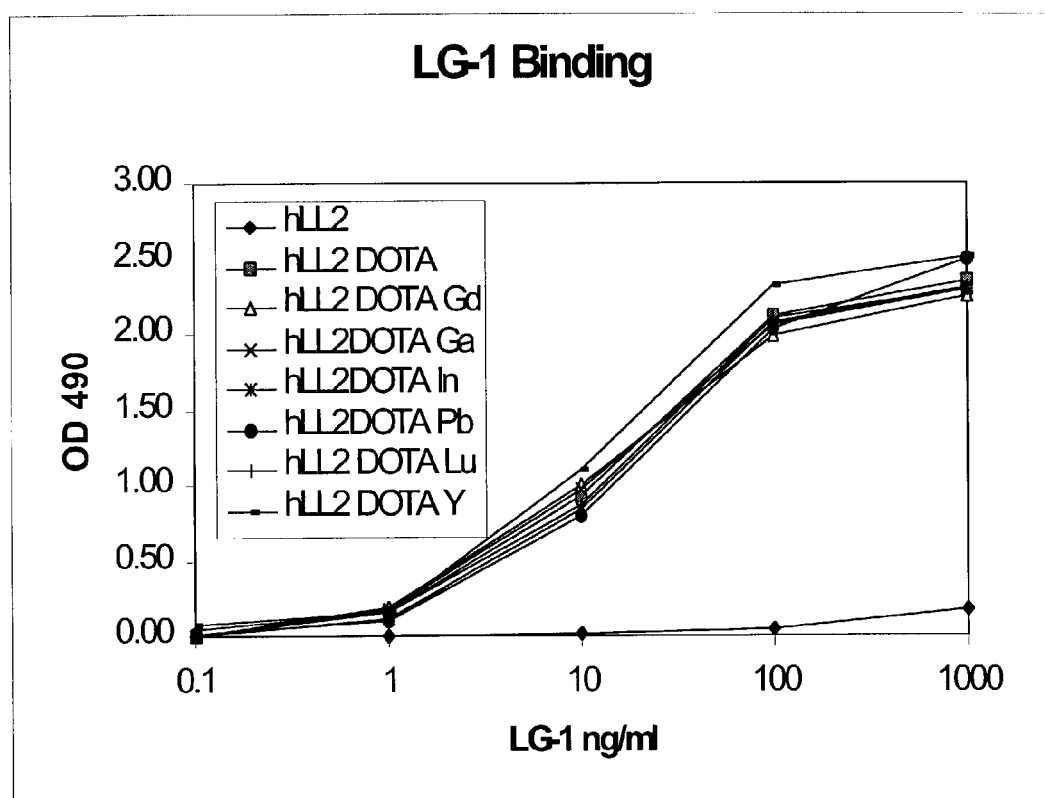
FIG. 1 depicts the binding of LG1 antibody to various DOTA-hLL2 metal complexes, as measured on an ELISA plate. Equivalent binding of the LG1 is seen with each metal complex, and with the DOTA-hLL2 containing no bound metal.

Immunocompetent mice were immunized mice with the macrocyclic chelate DOTA, previously coupled to a human-ized immunoglobulin (hIgG). A number of mice were injected and the harvested splenocytes fused with the mouse myeloma cell line SP2/0, according to a standard technique. A total of 1800 clones were screened by ELISA for reactivity with DOTA-conjugated hIgG and hIgG alone. Initially, 25 clones were identified as secreting an IgG that bound to the IgG-DOTA conjugate, but not to the IgG. After being sub-cloned three times, only one hybrid, termed LG1, remained positive and this was adapted to grow in serum-free media. Isotyping revealed that LG1 is an IgG$_2$b with a lambda light chain. LG1 was purified from culture supernatant with a yield of ~50 mg/liter of media. In ELISA, it has been shown to bind equally to free DOTA and to DOTA that has been loaded with several metals. These metals include gadolinium, gallium, indium, lead, lutetium and yttrium. Additionally, LG1 has a high affinity for a variety of DOTA compounds, showing strong reactivity starting at concentrations of ~1 ng/mL (~$10^{-9}$M), compared to previously produced anti-DOTA antibodies that had affinities measured in microgram amounts. Furthermore, based on an ELISA method to determine ligand binding affinity, the LG1 antibody is estimated to have an affinity of ~$10^{-10}$-$10^{-12}$ M towards many different metal-DOTA complexes (FIG. 1).

The terms antibody and antibody fragments are used interchangeably herein. Furthermore, as used herein, the term antibody may also be used to refer to bi-specific antibodies (bisAbs) or multi-specific antibodies (msAbs). The terms bisAb and msAb are used interchangeably herein. Antibody fragments are antigen binding portions of an antibody, such as F(ab')$_2$, F(ab)$_2$, Fab', Fab, and the like. The antibody fragments bind to the same antigen that is recognized by the intact antibody. For example, an anti-CD22 monoclonal antibody fragment binds to an epitope of CD22.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the hypervariable region.

The chelator 1,4,7,10-tetrazacyclododecane-N,N',N",N"'-tetraacetic acid (DOTA) is well-recognized in the art. As used herein, the phrase "a metal complex of DOTA" is used to mean a DOTA molecule that is bound to, or associated with a metal ion. Additionally, "metal" and "metal ion" are used interchangeably herein. The metal of the DOTA-metal complex may be any metal that is used to diagnose or treat diseases or pathological conditions in subjects. Furthermore, the metal of the DOTA-metal complex is selected from the group of all transition metals, group II metals, group IIIa, group IVa, Va, VIa, lanthanides and actinides.

As used herein, the term subject means any animal, especially a mammal, including a non-human primate or a human. The terms "subject," "organism," and "patient" may be used interchangeably.

In one embodiment, the metal of the metal-DOTA complex can be a radionuclide or a non-radioactive metal. Suitable metals of the metal-DOTA complex include copper-64, copper-67, gallium-67, gallium-68, zirconium-89, indium-111, gadolinium-157, scandium-47, yttrium-90, samarium-153, terbium-161, holmium-166, lutetium-177, lead-212, bismuth-212, bismuth-213, actinium-225 and actinium-227.

As the current invention contemplates, the DOTA molecule or complex that the LG1 antibody recognizes may or may not be linked or associated with any other molecule. At least one molecule of DOTA, but possibly more, may be either linked to, or incorporated into, a carrier molecule. Examples of carrier molecules include, but are not limited to, a protein, including small or large polypeptides, a polymer and antibodies. The carrier molecule may or may not elicit an immune response in an organism. However, the carrier molecule, or backbone, to which DOTA may be attached should be designed to be resistant to the effects of enzymes such as carboxypeptidases, aminopeptidases, and other peptidases present in serum. Suitable carrier molecules include bovine serum albumin, hLL2 (a humanized anti-CD22 monoclonal antibody), peptides and polymers.

In one aspect of the invention, DOTA is incorporated into a peptide at least once. When a peptide is used for the backbone, it can be constructed using some D-amino acids, and have its N- and C-termini blocked. The blocking can be general in nature, such as use of an alpha-amino acetyl-group for the N-terminus, and conversion of the C-terminus to an amide function. Alternatively, a DOTA chelate can be conveniently placed on either terminus of the peptide chain, and also protect the peptide from C- and N-terminus peptidases. It is well known that cyclization of peptides tends to increase serum half-lives and resistance to serum peptidases, and cyclized peptides as carrier backbones are within the scope of the invention.

A typical peptide containing more than one DOTA per backbone is Ac-Phe-Lys(DOTA)-Tyr-LyS(DOTA-NH$_2$ (SEQ ID NO: 5). It has been radiolabeled with $^{111}$In and shown to bind strongly to the LG1 mAb. It will be appreciated that numerous modifications to the size and other properties of this construct are facile to one skilled in the art of peptide synthesis. Alternative DOTA-containing peptides are exemplified by the following (underlined portions are disulfide cyclized):

A) Ac-Lys(DOTA)-Tyr-Lys(DOTA)-Tyr-Lys(DOTA)NH$_2$ (SEQ ID NO: 6)
B) Ac-Lys(DOTA)-Tyr-Lys(DOTA)-Tyr-Lys(DOTA)-Tyr-lys(DOTA)-NH$_2$ (SEQ ID NO: 7)
C) cyclo-Lys(DOTA)-D-Tyr-Lys(DOTA)-Tyr-Lys(DOTA)-Ala-
D) Ac-Cys(Acm)-Lys(DOTA)-D-Tyr-Ala-Lys(DOTA)-Cys(Acm)-NH2
E) Ac-Cys-Lys(DOTA)-D-Tyr-Ala-Lys(DOTA)-Cys(Acm)-NH2
F) Ac-Cys(Acm)-D-Lys(DOTA)-Tyr-Ala-Lys(DOTA)-Cys(Acm)-NH2
G) Ac-Cys-D-Lys(DOTA)-Tyr-Ala-Lys(DOTA)-Cys-NH2

The above peptide-bearing chelates may be synthesized routinely either manually or automatically depending upon peptide length, with either L- or D- amino analogs for each amino acid. Automatic syntheses may be performed conveniently using an Fmoc-based synthetic strategy to obviate any use of hydrogen fluoride. Generally, peptides are synthesized on acid sensitive resins such as 2-chlorotrityl (for C-terminal acids) or Sieber amide resin (for C-terminal amides), allowing each step of the peptide synthesis to be monitored. Epsilon nitrogen groups of lysine may be protected with the orthogonal protecting groups Fmoc and Abc to allow for the separate functionalization of each of nitrogens during synthesis. DOTA groups are conveniently added by reaction with the mono-acidic, tri-t-butyl ester of DOTA. This methodology was used to produce the bis-DOTA peptide Ac-Phe-Lys(DOTA)-Tyr-Lys(DOTA)-NH$_2$ (SEQ ID NO: 5) (MW$^+$1399) [IMP 236]. Cyclic derivatives are prepared as follows. Briefly, the synthesis is done on an acid sensitive resin (2-chlorotrityl) to allow the cleavage of the fully protected peptide from the resin with a C-terminal acid group. The synthesis starts with Fmoc-Ala-OH added to the resin, followed by the addition of Aloc-Lys(Fmoc)-OH. The tri-t-butyl DOTA is added to the lysine side chain and the alpha-abc group is removed using a palladium catalyst. Fmoc-Tyr(But)-OH followed by Aloc-Lys(Fmoc)-OH, tri-t-butyl DOTA, Fmoc-D-Tyr(But)-OH, Aloc-Lys(Fmoc)-OH, tri-t-butyl DOTA are added, with intermediate Abc or Fmoc protecting group cleavage reactions, as appropriate. The side chain protected peptide is cleaved from the resin with a mild acid treatment (1% TFA in CH$_2$Cl$_2$). The peptide is cyclized in a dilute DMF solution with diphenylphosphorylazide. The side chain protecting groups are finally removed and the peptide purified by reverse-phase HPLC.

The use of multivalent haptens starting with bivalent haptens and extending to haptens that have higher valencies is also contemplated in this invention. The superiority of radiolabeled bivalent haptens, compared to monovalent haptens, in pretargeting experiments has been described in several literature works. As used herein, the terms "multivalent haptens" and "bivalent haptens" are used interchangeably. Low molecular weight radiolabeled haptens used for radioimmunotherapy (RAIT) must not only bind well to pretarging Abs under in vivo targeting conditions, but they must also meet certain other criteria, including being stable enough not to dissociate free isotope during the short localization phase and during a substantially longer period where they remain attached to a tumor surface. A rapid clearance profile via the urine is preferred and an intact complex should ideally be excreted. Thus, the molecule that comprises the radiolabeled hapten must remain relatively hydrophilic. There should be no appreciable retention of the radiolabeled hapten in any non-targeted organ. The hapten should be capable of being labeled with metal at high specific activity, so that most hapten is associated with a metal (nuclide) atom. The chemical linkages binding the recognition and chelate-nuclide units to the backbone, and the backbone itself, must not be hydrolytically or enzymatically cleaved for the duration of the protocol. There needs to be an adequate separation of the recognition units of the hapten with >10 ångströms producing optimal recognition and binding.

Typical procedures for the production of radiolabeled DOTA-peptides incorporating, for example, Y-90 and Lu-177 are as follows. Of particular importance is the maximum specific activity achievable, which depends on the quality of the isotope. The radionuclide, obtained in an acidic solution, is treated with an excess of an acetate buffer, to a final pH of 4-6, and added to the DOTA-peptide conjugate, also in acetate buffer. All manipulations are carried out using acid-washed and metal-free components. The labeling mixture is heated at 45° C. for one hour and then allowed to cool to room temperature. Radiolabeled peptides are analyzed by RP-HPLC to determine incorporation, and are tested for binding to LG1, by mixing with a small excess of the LG1 mAb, and testing by analytical size-exclusion HPLC.

Non-radioactive metals are also of use in the invention. An example is gadolinium, which is a useful metal for magnetic resonance imaging. Similarly to the radiometals, a solution of non-radioactive gadolinium in acid is neutralized to pH 4-6 using excess ammonium acetate. The gadolinium added to the DOTA-peptide at an equimolar ratio of gadolinium to the DOTA moieties present. After a one-hour labeling time at 45° C., the added gadolinium is substantially bound to the DOTA-peptide.

The LG1 antibody was shown to bind equivalently well to the uncomplexed DOTA-hLL2 as to DOTA-hLL2 complexed with the metals gadolinium, gallium, indium, lead, lutetium and yttrium. These metals represent a diverse group in terms of binding properties, valency, coordination number and stereochemistry. All metal-DOTA-hLL2 complexes tested bound to LG1 (FIG. 1). This suggests that the LG1 mAb is able to recognize the DOTA ring, which would allow the LG1 Ab to recognize a greater diversity of metal-DOTA complexes.

To determine the essential features that are important to elicit LG1 binding, labeled DOTA (indium-111) was linked to a hapten, via lysine residues, on either the alpha (DOTA-Lys(HSG)-D-Tyr-Lys(HSG)-NH$_2$) or epsilon (biotin-D-Phe-D-Lys[DOTA]) positions of one of the DOTA carboxy groups. LG1 did bind the epsilon-linked indium-DOTA, but not the alpha-linked indium DOTA. Furthermore, LG1 did not bind to indium-DOTA alone. These results indicate that LG1 requires the DOTA ring and its substitution onto an alkyl amine that is non-substituted at its alpha position, while the identity of the metal is not crucial. Thus, the antibody of the current invention is "universal" in that it may bind to any DOTA-metal complex with a pendant N-alkylacetamide group, regardless of the type of metal with which DOTA is complexed. As used herein, the phrases "universal anti-DOTA antibody" or "universally binds" are used to mean an antibody that binds to any DOTA or DOTA-metal complex with a pendant N-alkylacetamide group.

The LG1 Ab of the current invention is monoclonal in nature. Also, the LG1 Ab may be chimeric, humanized, human or deimmunized.

As used herein, deimmunized antibodies are antibodies with a reduced immunogenicity, i.e. antibodies that activate T-cells endogenous to the subject to a lesser extent than a comparable monoclonal, chimeric, humanized or human antibody. This may be necessary because monoclonal, chimeric, humanized and even human antibodies can still elicit a T-cell response, due to presence of T-cell epitopes on the antibodies. In particular, complementarity-determining region residues or framework residues of antibodies can elicit an anti-idiotypic response by the host. This possibility of T-cell activation and response can also be exacerbated during the identification of higher affinity antibodies by affinity maturation. Examples of the ways in which decreased immunogenicity manifests itself include, but are not limited to, fewer T-cells being activated, or weaker binding of the T-cells to the immunogenic portion of the antibody. For preparation of deimmunized antibodies, epitopes recognized by T-cells are first identified. Briefly, the discrete number of MHC class II allotypes that occur in the population are identified and used to screen all possible 13-mer peptide fragments contained in the antibody to be deimmunized. Peptide binding grooves for each class II allotype are presented with peptides to determine, for each, a series of conformational binding scores that can be matched against a database of MHC Class II models. Biologically active T-cell epitopes achieve high binding scores while epitopes predicted to not engender a T-cell response give low binding scores. Modified sequences of the 13-mer peptides are subsequently designed to contain single amino acid substitutions to eliminate epitopes that can be recognized by the T-cells. Candidate variant antibodies are expressed and assayed, and lead deimmunized antibody candidates are selected.

In one embodiment, the LG1 Ab of the current invention may be engineered to possess a label. The labels can be used for, among other things, tracking the location and clearance of the administered msAbs in the subject. Examples of labels that the Ab may possess include, but are not limited to, a labeling ligand such as the biotin-streptavidin complex and radioisotopes. An example of a radiolabel used for tracking purposes, includes, but is not limited to, technetium. For example, a Tc-99m-labeled DOTA can be administered to the subject following administration of the msAbs. The subject is then scanned with a gamma camera which produces single-photon emission computed tomographic images and defines the lesion or tumor site. Additionally, the therapeutic radioisotope associated with DOTA can also be used for tracking purposes as some therapeutic radioisotpoes can emit gamma radiation useful for tracking purposes.

The invention also provides for a bi-specific or multi-specific Ab comprising a target arm that binds to a tissue antigen, and a capture arm that binds to DOTA, or a metal complex of DOTA. As used herein, "target arm" is used to mean the portion of the bi-specific or multi-specific Ab that binds to an antigen present in or on, or associated with, a targeted tissue. Furthermore, to treat infectious agents, the target arm can also bind to pathogens, including, but not limited to viruses, bacteria, fungi, parasites and/or prions.

As used herein, the term tissue is used to mean a tissue as one of ordinary skill in the art would understand it to mean. As envisioned in the current application, tissue is also used to mean individual cells or groups of cells, or cell cultures, of a bodily tissue or fluid (e.g. blood cells). Furthermore, the tissue may be within a subject, or biopsied or removed from a subject. The tissue may also be a whole or any portion of a bodily organ. Additionally, the tissue may be "fresh" in that the tissue would be recently removed from a subject without any preservation steps between the excision and the methods of the current invention. The tissue may also have been preserved by such standard tissue preparation techniques including, but not limited to, freezing, quick freezing, paraffin embedding and tissue fixation, prior to application of the methods of the current invention.

The antigen may be attached externally to a cell or tissue, or part of the cell-surface membrane, or may be a GPI-anchored protein, or may be internal to a cell. Additionally, the antigen may be a pathogen in proximity to the diseased tissue, thus the antigen does not necessarily have to be directly contacting or integrated with the cell. The antigen may be associated with fluids including, but not limited to, any part of whole blood, lymphatic fluid or cerebrospinal fluid. Furthermore, the antigen may be present in normal, abnormal, diseased or necrotic cells or tissue. The antigen may also have specific characteristics, such as a distinct cell-surface-associated antigen, or the antigen may have general characteristics that are shared by more than one tissue or cell type. For example, $\beta$1-integrin is an extracellular cell adhesion molecule shared by a variety of normal or diseased tissue that is antigenic and would be considered a target site within the context of the current invention.

As used herein, the "capture arm" is used to mean the portion of the msAb that recognizes or binds to DOTA.

The msAbs of the present invention include, but are not limited to, IgG×IgG, IgG×F(ab')$_2$, IgG×Fab', IgG×scFv, F(ab')$_2$×F(ab')$_2$, Fab'×F(ab')$_2$, Fab'×Fab', Fab'×scFv and scFv×scFv bi-specific monoclonal antibodies (bsmAbs). Also, species such as scFv×IgG×scFv and Fab'×IgG×Fab', scFv×F(ab')$_2$×scFv and Fab'×F(ab')$_2$×Fab' are included. Advantageously, site-specific attachment sites on the IgG or F(ab')$_2$ of one or both monoclonal antibodies (mAbs) can be utilized, such as an engineered carbohydrate or an engineered or liberated free thiol group.

Multi-specific Abs containing LG1/DOTA secondary recognition arms can be prepared by chemical cross-linking, quadroma production or constructed using molecular biology. The specific agents mentioned in this discussion are not meant to be limitative, but are exemplary of the numerous msAb formats that are possible. For targeting, mAbs binding to well-known antigenic targets are advantageously used. Antigenic targets include, but are not limited to, MHC complex components, receptors and tumor antigens. Specifically, such target antigens include carcinoembryonic antigen (CEA), 17-1A, colon-specific antigen P, epithelial glycoprotein, HER-2/neu, epidermal growth factor receptor, CD19, CD20, CD22 and CD74. Any targeting mAb can be used. When preparing msAbs chemically, IgG-1×IgG-2-type conjugates can be prepared (where IgG-1 is the targeting mAb and IgG-2 is the LG1 mAb), as can IgG-1×F(ab')$_2$-2; F(ab')$_2$-1×IgG-2; F(ab')$_2$-1×F(ab')$_2$-2; IgG-1×Fab'-2; F(ab')$_2$-1×Fab'-2; Fab'-1×Fab'-2; Fab'-1×F(ab')$_2$-2; and Fab'-1×IgG-2. Sub-fragments smaller than Fab's can also be used, including sFvs, as can alternatively prepared fragments such as Fabs. For instance, a mAb directed towards carcinoembryonic antigen (CEA), anti-CEA F(ab')$_2$, having an engineered light-chain carbohydrate can be oxidized and converted using a hydrazide-maleimide cross-linker to a derivatized anti-CEA F(ab')$_2$ having at least one pendant maleimide group per each light chain. This species is coupled to LG1-Fab'-SH at a 1:2 molar ratio or greater, such that an anti-DOTA-Fab'×anti-CEA-F(ab')$_2$-anti-DOTA-Fab' conjugate is produced. The resultant msAb is bivalent with respect to the target tissue and DOTA. Quadromas can also be made that secrete IgG-1×IgG-2 msAbs.

Using standard techniques of molecular biology, instead of chemistry, numerous constructs having different molecular sizes and valencies to each antigen (e.g. to CEA and DOTA) can be prepared. After the initial raising of the LG1 Ab, a msAb containing a capture arm that binds to DOTA or a metal complex of DOTA, they may be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized mAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

These various constructs having different molecular sizes and valencies to each antigen include scFv anti-CEA×Fab' anti-DOTA (divalent to CEA and monovalent to DaTA), and anti-CEA lgG×2 scFv anti-DOTA (divalent construct to both antigens). Briefly, the variable sequence for MN-14 anti-CEA has already been determined, and identical procedures will establish the variable region sequence of the LG1 mAb. The single chain structures of hMN-14 (scFv hMN-14) and LG1 (scFv LG1) are constructed by PCR, using DNA vectors containing the VH and VK sequences of the two antibodies as templates. The constructs have the configuration VL-(GGGGS)$_3$-VH (SEQ ID NO: 8). The hMN-14 and LG1 V-region sequences are obtained from vectors according to well-known methods. The scFv structures for both hMN-14 and LG1 are needed for the construction of msAb with different antigenic valencies. All scFv sequences are sequenced to ensure no mutations or frame-shifts are introduced before their being used for msAb construction. The scFv hMN-14 sequence is ligated in-frame to the CH1 domain of LG1 heavy chain sequence, with the resulting configuration of LG1 VH-CH1-scFv hMN-14. This sequence is sub-cloned in an expression vector containing the kappa chain sequence of LG1. The resultant expression vector, LG1 Fab-scFvhMN-14pdHL2, when transfected into the appropriate host cells, produces a fusion protein with monovalent specificities for hMN-14 and LG1, respectively. Other methods of producing fusion proteins are discussed further in U.S. Ser. Nos. 09/337,756 and 60/220,782, with each disclosure being hereby incorporated by reference.

The scFv hMN-14 sequence is similarly ligated in-frame to the CK domain of LG1 light chain, with the resultant light chain sequence having the configuration of LG1 VK-CK-scFv hMN-14. The fusion light chain sequence is used to replace the LG1 light chain sequence in the vector LG1Fab-scFvhMN-14pdHL2. The resultant expression vector, LG1Fab-[scFvhMN-14]$_2$pdHL2 encodes the expression of a fusion protein of a LG1 Fab, attached to the C-terminal ends of MN-14 Fd. An alternate construct comprises a human IgG$_1$ for hMN-14. Attached to the C-terminal ends of the heavy chain CH3 domains are two scFvs for LG1. Construction of the expression vector encoding the fusion protein is achieved by recombinantly inserting the scFv sequence for LG1 in-frame to the sequence encoding the CH3 domain in the hMN-14pdHL2 expression vector. The resultant expression vector for the fusion msAb is designated as hMN-14IgG-[scFv LG1]$_2$pdHL2.

The msAbs are cloned into an amplifiable expression vector, pdHL2. The expression vectors for msAb fusion proteins are transfected into SP2/0 cells by electroporation using well-known literature conditions. Transfected cells are selected with 0.1 µM Methotrexate (MTX), and clones surviving selection are tested for antibody production by ELISA assays. Positive clones are further tested for specific anti-CEA and anti-DOTA binding activities by ELISA. Purification of LG1Fab-scFvhMN-14 and LG1Fab-[scFvhMN-14]$_2$ lacking the Fc portion is accomplished by affinity chromatography using a Protein L column, which interacts with kappa chains. The hMN-14IgG-[scFvLG1]$_2$ is purified on a Protein A column following standard procedures. Further purification of msAbs is accomplished by FPLC using a SP Sepharose column (Pharmacia, Piscataway, N.J.). The assembly patterns and polymerization states of the msAbs are then determined by fractionating the purified msAbs on 5% phosphate gels. To verify the absence of aggregates in the msAbs, purified proteins are fractionated by FPLC using a Superose 6 column. The binding affinities of the msAbs are evaluated by competition ELISA assays. Varying concentrations of msAbs or control mAbs (MN-14 IgG, MN-14 Fab, LG1 IgG, and LG1 Fab) are mixed with a fixed amount of HRP-conjugated MN-14 or LG1 and incubated in microwells coated with either CEA or IgG-DOTA. The residual binding of HRP-MN-14 or -LG1 is determined by standard ELISA assay. Clones confirmed to secrete msAb of expected specificity are subjected to amplification by step-wise increase of the concentration of MTX in the cell culture media.

Fully human antibodies can be obtained from transgenic non-human animals. See, e.g., Mendez et al., *Nature Genetics*, 15: 146-156 (1997); U.S. Pat. No. 5,633,425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics*, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is islolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., VaughiFetal., *Nat. Biotechnol.*, 14: 309-314 (1996). An scFv library with a large repertoire can be constructed by isolating V-genes from non-immunized human donors using PCR primers corresponding to all known V heavy-chain ($V_H$) and V light-chains ($V_\kappa$ and $V_\lambda$) gene families. Following amplification, the $V_\kappa$ and $V_\lambda$ pools are combined to form one pool. These fragments are ligated into a phagemid vector. The scFv linker, $(Gly_4\text{-}Ser_1)_3$ (SEQ ID NO: 8), is then ligated into the phagemid upstream of the V light-chain ($V_L$) fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., *Biotechnology*, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J. Cancer*, 78: 181-188 (1998); Osbourn et al., *Immunotechnology*, 2:. 181-196 (1996).

The LG1 Ab, or the msAb containing a capture arm that binds to DOTA may be chimerized or humanized by known techniques or fully human. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce msAbs. For example, bi-specific antibodies and antibody fragments can be produced in the milk of transgenic livestock. See, e.g., Colman, A., *Biochem. Soc. Symp.*, 63: 141-147, 1998; and U.S. Pat. No. 5,827,690. Two DNA constructs are prepared which contain, respectively, DNA segments encoding paired immunoglobulin heavy and light chains. The fragments are cloned into expression vectors which contain a promoter sequence that may be expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. The inserted fragment may be flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. For the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing msAbs include engineered recombinant Abs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAbs), also called diabodies, can be produced in mammalian cells using recombinant methods. See, e.g., Mack et al., *Proc. Nati. Acad. Sci.*, 92: 7021-7025, 1995. For example, bscAbs are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4-Ser_1)_3$ (SEQ ID NO: 8) linker, and the second step joins the $V_L$ and $V_H$ amplicons. Each single chain molecule is then cloned into a bacterial expression vector. Following amplification, one of the single-chain molecules is excised and sub-cloned into theother vector, containing the second single-chain molecule of interest. The resulting bscAb fragment is sub-cloned into an eukaryotic expression vector. Functional protein expression can be obtained by transfecting the vector into chinese hamster ovary cells. Bi-specific fusion proteins are prepared in a similar manner. Bi-specific single-chain antibodies and bi-specific fusion proteins are included within the scope of the present invention.

Bi-specific fusion proteins linking two or more different single-chain antibodies or antibody fragments are produced in similar manner as discussed above. Recombinant methods can be used to produce a variety of fusion proteins. For example a fusion protein comprising a Fab fragment derived from a humanized monoclonal anti-CEA antibody and a scFv derived from a murine anti-diDTPA can be produced. A flexible linker, such as $(GGGS)_3$ (SEQ ID NO: 9), which is a trimer of glycyl-glycyl-glycyl-serine, connects the scFv to the constant region of the heavy chain of the anti-CEA antibody. Alternatively, the scFv can be connected to the constant region of the light chain of hMN-14. Appropriate linker sequences necessary for the in-frame connection of the heavy chain Fd to the scFv are introduced into the $V_\lambda$ and $V_\kappa$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an anti-CEA antibody. The resulting vector can be used to transfect mammalian cells for the expression of the bi-specific fusion protein.

Large quantities of bscAb and fusion proteins can be produced using *Escherichia coli* expression systems. See, e.g., Zhenping et al., *Biotechnology*, 14: 192-196, 1996. A functional bscAb can be produced by the coexpression in *E. coli* of two "cross-over" scFv fragments in which the $V_L$ and $V_H$ domains for the two fragments are present on different polypeptide chains. The $V_L$ and $V_H$ domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the *E. coli* alkaline phosphatase promoter which is inducible by phosphate starvation. Alternatively, single-chain fusion constructs have successfully been expressed in *E. coli* using the lac promoter and a medium consisting of 2% glycine and 1% Triton X-100. See, e.g., Yang et al., *Appl. Environ. Microbiol.*, 64: 2869-2874, 1998. An *E. coli*, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., Staphylococcal protein A chromatography.

Functional bscAb and fusion proteins also can be produced in the milk of transgenic livestock. See, e.g., Colman, A., *Biochem. Soc. Symp.*, 63: 141-147, 1998; U.S. Pat. No. 5,827,690. The bscAb fragment, obtained as described above, is cloned into an expression vector containing a promoter sequence that can be expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. The inserted bscAb may also be flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.*, 13: 1090-1093, 1995; Fiedler et al., *Immunotechnology*, 3: 205-216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic recticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods,* 212: 149-160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.,* 42: 177 (1988); Bei et al., *J. Immunol. Methods,* 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods,* 212: 149-160 (1998). The bscAb fragment, obtained as described above, is cloned into an expression vector containing the *Drosphila* metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

The present invention can be used in a variety of methods that utilize radioisotopes as a therapeutic or diagnostic agent for such diseases as cancer, infections and inflammations. For example, the LG1 antibody of the current invention can be used for RAIT therapy, whereby a radionuclide is specifically delivered to a tumor, via a DOTA-metal complex, whereby the metal is a radionuclide effective for treating tumors. The present invention can also be used in other disease therapies that involve radionuclides, such as thyroid cancer therapy (delivering $^{131}I$ or $^{125}I$), bone cancer therapy (delivering, among others, $^{89}Sr$, $^{85}Sr$, $^{153}Sm$, $^{32}P$).

The present inventive antibodies or antibody fragments can be used in a method of photodynamic diagnosis or therapy. In the diagnostic method, a diagnostic agent is injected, for example, systemically, and laser-induced fluorescence can be used by endoscopes to detect sites of cancer which have accreted the light-activated agent. For example, this has been applied to fluorescence bronchoscopic disclosure of early lung tumors (Doiron et al., *Chest* 76:32, 1979), incorporated herein by reference. In another example, the inventive antibodies and antibody fragments can be used in single photon emission. For example, a Tc-99m-labeled diagnostic agent can be administered to the subject following administration of the msAbs. The subject is then scanned with a gamma camera which produces single-photon emission computed tomographic images and defines the lesion or tumor site.

The present invention also can be used in a method for photodynamic therapy. In this methodology, a photosensitizer, for example a hematoporphyrin derivative such as dihematoporphyrin ether is administered to the subject. Anti-tumor activity is initiated by the use of strong red light, for example, at 630 nanometers wavelength. Alternate photosensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (A1SPc) and lutetium texaphyrin (Lutex).

The present invention may also be used in a method for gadolinium neutron capture therapy, which is described in De Stasio et al.; *Cancer Research;* 61:4272-4277 (2001), and is hereby incorporated by reference. Briefly, gadolinium-155 and 157 have two of the largest thermal neutron capture cross-sections of any nuclide, measured in units of barns, representing the ability of a nuclide to capture a neutron when exposed to a neutron beam of appropriate energy. The higher the thermal neutron capture cross-section, the less material that will need to be concentrated in a tissue to effect a capture reaction. Also, a more favorable therapeutic ratio may be achieved with a greater difference between the capture rates of the capture nuclide (gadolinium) and nuclides found in abundance in tissue, such as carbon, nitrogen, oxygen, phosphorus, chloride, and sulfur. The LG1 antibody in the present invention binds to gadolinium-DOTA complexes as well as it binds to the yttrium-DOTA complexes, and may therefore be used for targeting gadolinium to sites of diseases.

The present invention can be used in Boron Neutron Capture Therapy (BNCT) protocols. BNCT is a binary system designed to deliver ionizing radiation to tumor cells by neutron irradiation of tumor-localized boron-10 atoms. BNCT is based on the nuclear reaction which occurs when a stable isotope, isotopically enriched B-10 (present in 19.8% natural abundance), is irradiated with thermal neutrons to produce an alpha particle and a Li-7 nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of boron-10 at tumor sites, while leaving non-target organs essentially boron-free. Compositions and methods for treating tumors in patients using pre-targeting msAbs for BNCT are described in U.S. Ser. No. 09/205,243 and can easily be modified in accordance with the present invention. Additionally, other elements are suitable for neutron capture reactions, such as uranium or gadolinium. Gadolinium neutron capture therapy is further described in De Stasio et al., Cancer Research, 61:4272-4277 (2001), which is hereby incorporated by reference.

The current invention also provides kits comprising an antibody to an antibody or antibody fragment that binds to 1,4,7,10-tetrazacyclododecane-N,N',N",N'"-tetraacetic acid (DOTA),which is bound to an alkyl-amino group through one of its pendant carboxyl groups and an agent selected from the group consisting of 1,4,7,10-tetraazacyclododecane-N,N',N",N'"-tetraacetic acid (DOTA), a metal complex of DOTA, a polypeptide construct comprising DOTA, and a polypeptide comprising a metal complex of DOTA.

The msAb of the kit may be monoclonal or polyclonal in nature. Furthermore, both the target arm and the capture arm can be monoclonal.

The msAb of the kit may be engineered to possess a label. Examples of labels that the msAb may possess include, but are not limited to, a labeling ligand such as a biotin-streptavidin complex and radioisotopes.

One or both arms of the msAb of the kit may be chimeric, human, humanized, or deimmunized.

The kit as provided by the current application may also include a clearing composition that will clear the unbound msAb from the tissue. One suitable clearing agent is a glycosylated anti-idiotypic Fab' fragment targeted against the disease targeting arm(s) of the msAb. In this embodiment, a msAb is given and allowed to accrete in targets to its maximum extent. To clear the residual msAb, an anti-idiotypic Ab to the target Ab is given as a glycosylated Fab' fragment. The clearing agent binds to the msAb in a monovalent manner, while its appended glycosyl residues direct the entire complex to the liver, where rapid metabolism takes place. Then the (radiolabeled)-chelate therapeutic is given to the patient. Clearing agents are discussed in greater detail in U.S. Ser. Nos. 09/314,135 and 09/337,756, with each disclosure being hereby incorporated by reference.

The present invention provides isolated nucleic acid molecules comprising a polynucleotide encoding the LG1 variable heavy chain ($V_H$) and variable light chain ($V_L$) having the amino acid sequences shown in FIG. 3 (SEQ ID NO:2) and FIG. 4 (SEQ ID NO:4), respectively.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of the DNA sequence. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The nucleotide sequence of the LG1 $V_H$ reveals a 354 amino acid polypeptide containing three complentarity determining regions (CDRs), shown in FIG. 3. The nucleotide sequence of the LG1 $V_L$ reveals a 324 amino acid polypeptide containing three complentarity determining regions (CDRs), shown in FIG. 4.

Thus, one aspect of the invention provides an isolated nucleic acid molecule comprising a polynucleotide having a nucleotide sequence selected from the group consisting of: (a) a nucleotide sequence encoding the LG1 $V_H$ having the complete amino acid sequence in SEQ ID NO:2; (b) a nucleotide sequence encoding the LG1 $V_L$ polypeptide having the complete amino acid sequence in SEQ ID NO:4; (c) the nucleotide sequence of SEQ ID NO:1; (d) the nucleotide sequence of SEQ ID NO:3 and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), or (d) above, or a polynucleotide which hybridizes under stringent hybridization conditions to a polynucleotide in (a), (b), (c) or (d) above. This polynucleotide which hybridizes does not hybridize under stringent hybridization conditions to a polynucleotide having a nucleotide sequence consisting of only A residues or of only T residues.

By "stringent hybridization conditions" is intended overnight incubation at 42 degrees C. in a solution: 50% formamide, 5.times SSC (150 mM NaCl, 15 mM trisodium citrate), 50 mM sodium phosphate (pH7.6), 5 times Denhardt's solution, 10% dextran sulfate, and 20 μg/ml denatured, sheared salmon sperm DNA, followed by washing the filters in 0.1 times SSC at about 65 degrees C. By a polynucleotide which hybridizes to a portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers.

By a polynucleotide having a nucleotide sequence at least, for example, 95% "identical" to a reference nucleotide sequence encoding an LG 1 $V_H$ polypeptide is intended that the nucleotide sequence of the polynucleotide is identical to the reference sequence except that the polynucleotide sequence may include up to five point mutations per each 100 nucleotides of the reference nucleotide sequence encoding the LG1 $V_H$ polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97% 98%, 99% or even 100% identical to, for instance, the nucleotide sequence shown in FIG. 3 or FIG. 4 can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman (Advances in Applied Mathematics 2:482-489 (1981)) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Of course, due to the degeneracy of the genetic code, one of ordinary skill in the art will immediately recognize that a large number of the nucleic acid molecules having a sequence at least 90%, 95%, 96%, 97%, 98% or 99% identical to the nucleic acid sequence of the deposited DNA or the nucleic acid sequence shown in FIG. 3 (SEQ ID NO:1) will encode a polypeptide "having DOTA binding activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having DOTA binding activity. This is because the skilled artisan is fully aware of amino acid substitutions that are either less likely or not likely to significantly effect binding or folding(e.g., replacing one aliphatic amino acid with a second aliphatic amino acid). For example, Table 1 lists common substitute amino acids that possess similar properties.

In another aspect, the preferred embodiments of the present invention provide an antibody reactive with an epitope comprised of the macrocyclic ring 1,4,7,10,-tetraazacyclododecane-N,N,N,N-tetraacetic acid (DOTA), or a metal complex thereof, an aminoalkyl moiety, and about one to seven amino acids (AAs), bound to said aminoalkyl moiety.

In a preferred embodiment, the aminoalkyl moiety is a lysine residue in a peptide, polypeptide, polymeric or protein structure wherein the lysine residue is in the L-configuration and wherein the aminoalkyl moiety is a (—CH$_2$—)$_n$, where n is an integer from one to twenty. In a preferred embodiment, the polymeric structure is a polyamino acid or a dendrimer, wherein the polyamino acid is a co-polymer comprising lysine, tyrosine, phenylalanine, glutamic acid, glycine, alanine or histidine sub-units and the dendrimer is a generation dendrimer from zero to five.

As used herein, the term "generation dendrimer" relates to the size of the dendrimer being described. For example, N[(CH$_2$CH$_2$)NH$_2$]$_3$ can be a dendrimeric core—generation zero. If each of the three primary amino groups are reacted with six more units of —CH$_2$CH$_2$NH$_2$ you would get N[(CH$_2$CH$_2$)N]$_3$[—CH$_2$CH$_2$NH$_2$]$_6$. In this case, one would now have six free amino groups on the growing dendrimer. This would be generation one. If all six free amino groups are reacted with 12 new —CH$_2$CH$_2$NH$_2$ units, one would obtain a molecule N[(CH$_2$CH$_2$)N]$_3$[—CH$_2$CH$_2$NH$_2$]$_6$(CH$_2$CH$_2$NH$_2$)$_{12}$; a generation two dendrimer. Hence the dendrimer can be grown in distinct steps with each additional substitution level representing a new "generation."

In another preferred embodiment, the complexed metal is selected from the group of scandium, manganese, iron, cobalt, copper, gallium, yttrium, zirconium, technetium, indium, samarium, gadolinium, terbium, holmium, lutetium, rhenium, lead, bismuth and actinium.

The amino acids which comprise the about one to seven amino acids are selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

In a preferred embodiment, the amino acid sequence is:

(a) [epsilon-DOTA]-lysyl-AA1-AA2-AA3, and wherein the residues AA1, AA2 and AA3 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(b) AA1-AA2-AA3-[epsilon-DOTA]-lysyl- and wherein the residues AA1, AA2 and AA3 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(c) [epsilon-DOTA]-lysyl-AA1-AA2, and wherein the residues AA1 and AA2 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(d) AA1-AA2-[epsilon-DOTA]-lysyl- and wherein the residues AA1 and AA2 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(e) [epsilon-DOTA]-lysyl-AA1, and wherein the residue AA1 is selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(f) AA1-[epsilon-DOTA]-lysyl- and wherein the residue AA1 is selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(g) AA1-AA2-AA3-[epsilon-DOTA]-lysyl-AA4-AA5-AA6, and wherein the residues AA1-AA6 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(h) AA1-AA2-AA3-[epsilon-DOTA]-lysyl-AA4-AA5, and wherein the residues AA1-AA5 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(i) AA1-AA2-AA3-[epsilon-DOTA]-lysyl-AA4, and wherein the residues AA1-AA4 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(j) AA1-[epsilon-DOTA]-lysyl-AA2-AA3-AA4, and wherein the residues AA1-AA4 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(k) AA1-AA2-[epsilon-DOTA]-lysyl-AA3-AA4-AA5, and wherein the residues AA1-AA5 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(l) AA1-AA2-[epsilon-DOTA]-lysyl-AA3-AA4, and wherein the residues AA1-AA4 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(m) AA1-AA2-[epsilon-DOTA]-lysyl-AA3, and wherein the residues AA1-AA3 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

(n) AA1-[epsilon-DOTA]-lysyl-AA2, and wherein the residues AA1 and AA2 are selected from the group of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine;

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The present invention also relates to a method of treating or diagnosing a pathological state in a patient comprising administering an antibody that binds to DOTA with a pendant N-alkylacetamide group or a metal complex of DOTA, wherein the DOTA-metal complex has a pendant N-alkylacetamide group, and administering an agent comprising 1,4,7,10-tetraazacyclododecane-N,N',N'',N'''-tetraacetic acid (DOTA).

The method of the current invention may be carried out in vivo, in vitro or in situ in or on a tissue of the patient.

EXAMPLES references cited herein are hereby incorporated herein by reference in their entireties.

A) Complexation of Various Metals to DOTA-hLL2 Immunoconjugate

The immunogen used for the generation of the anti-DOTA antibody is the yttrium complex of the DOTA conjugate of the humanized LL2 antibody. This conjugate had previously been shown to exhibit a strong immune response when injected into normal rabbits, and its preparation is detailed in Example 2, below.

Example 1

Preparation of hLL2-DOTA Conjugate

Humanized LL2 mAb is sequentially buffer-exchanged with 20 mM DTPA/0.25 M ammonium acetate, pH 7.0, 0.25 M ammonium acetate, pH 7.0, and 0.1 M potassium phosphate-0.1 M sodium bicarbonate, pH 8.5 in a series of diafiltrations. Activated DOTA is prepared (45 min at 4° C.) using a mixture of DOTA, sodium bicarbonate, N-hydroxysulfosuccinimide and 1-ethyl-(3,3-dimethylamino)propyl carbodiimide in 10:30:10:1 molar ratios. Activated DOTA is then added to hLL2 in ~90-fold molar excess, the pH of the solution is re-adjusted to 8.27, and the solution is gently stirred at 4° C. for 18 h. The conjugation mixture is then subjected to a series of diafiltrations with 0.25 M ammonium acetate pH 7.0 and 0.25 M ammonium acetate, pH 5.4. The final product, hLL2-DOTA conjugate, is sterile-filtered and stored at 4° C. The DOTA content is determined by a known metal-binding assay (Meares, C.F., et al. Anal. Biochem. 142:68-78, 1984). Briefly, this involves reacting a known amount of the conjugate with a known excess of indium acetate spiked with radioactive indium, and determining the percent incorporation of indium into the conjugate. This average DOTA molar substitution ratio for the above conditions is determined to be 2.8.

Example 2

Preparation of an Yttrium Complex of the hLL2-DOTA Conjugate

For this, a DOTA conjugate of humanized LL2, with an average DOTA-to-hLL2 molar substitution ratio of 2.8-to-1 is used. A 49 mM solution of yttrium chloride ($YCl_3$) in 50 mM hydrochloric acid is prepared using yttrium chloride hexahydrate (of 99.999% purity). An aliquot of this $YCl_3$ solution (0.05 mL) is buffered with 0.3 mL of 0.25 M ammonium acetate pH 5.4. The DOTA conjugate of hLL2 (2 mL; 16.7 mg) is mixed with 0.238 mL of the buffered yttrium (approximately 15-fold molar excess) and heated at 45° C. for 30 minutes. This is followed by an additional 15-minutes of heating, subsequent to a DTPA-quench, using 0.248 mL of 0.1 M DTPA pH 6.7. The solution is cooled, and purified on two successive spin-columns ("centrifuged size-exclusion chromatography") of Sephadex G50/80 in 0.1 M sodium acetate pH 6.5. The final eluate is sterile-filtered. Matrix-assisted laser desorption ionization [MALDI] mass spectral analyses of both the uncomplexed hLL2-DOTA conjugate and yttrium-chelated conjugate gives a mass difference of 651 Daltons (151,837 for hLL2-DOTA versus 152,488 for hLL2-DOTA-yttrium), with an error rate of 0.2% in this mass range.

Example 3

Preparation of a Lutetium Complex of the hLL2-DOTA Conjugate

A 49 mM solution of lutetium chloride in 50 mM hydrochloric acid is prepared using anhydrous lutetium chloride (99.99% purity). The metal complexation procedure, involving hLL2-DOTA conjugate and buffered lutetium chloride, and the purification are carried out as detailed in Example 2 for yttrium. MALDI mass spectral analyses of both the uncomplexed hLL2-DOTA conjugate and lutetium-chelated conjugate gives a mass difference of 555 Daltons (151,837 for hLL2-DOTA versus 152,392 for hLL2-DOTA-lutetium), with an error rate of 0.2% in this mass range.

Example 4

Preparation of an Indium Complex of the hLL2-DOTA Conjugate

A 47 mM solution of indium chloride in 50 mM hydrochloric acid is prepared using anhydrous indium chloride (99.999% purity). The complexation procedure, involving hLL2-DOTA conjugate and buffered indium chloride, and the purification are carried out as detailed in Example 2 for yttrium. MALDI mass spectral analyses of both the uncomplexed hLL2-DOTA conjugate and indium-chelated conjugate gives a mass difference of 231 Daltons (151,837 for hLL2-DOTA versus 152,068 for hLL2-DOTA-In), with an error rate of 0.2% in this mass range.

Example 5

Preparation of a Lead Complex of the hLL2-DOTA Conjugate

A 47 mM solution of lead chloride in 100 mM nitric acid is prepared using anhydrous lead chloride (99.999% purity). The complexation procedure, involving hLL2-DOTA conjugate and buffered lead nitrate, and the purification are carried out as detailed in Example 2. MALDI mass spectral analyses of both the uncomplexed hLL2-DOTA conjugate and lead-chelated conjugate gives a mass difference of 571 Daltons (151,837 for hLL2-DOTA versus 152,408 for hLL2-DOTA-Pb), with an error rate of 0.2% in this mass range.

Example 6

Preparation of a Gadolinium Complex of the hLL2-DOTA Conjugate

A 51 mM solution of gadolinium chloride in 50 mM hydrochloric acid is prepared using anhydrous gadolinium chloride (>99.9% purity). The complexation procedure, involving hLL2-DOTA conjugate and buffered gadolinium chloride, is carried out as detailed in Example 2, except that the molar excess of the metal used was 50-fold. The product is purified by two successive spin-columns on Sephadex G50/80 equilibrated in 0.1 M sodium phosphate buffer pH 7.3.

Example 7

Preparation of a Gallium Complex of the hLL2-DOTA Conjugate

A 50 mM solution of gallium chloride in 50 mM hydrochloric acid is prepared using anhydrous gallium chloride (99.999% purity). The complexation procedure, involving hLL2-DOTA conjugate and buffered gallium chloride, is carried out as detailed in Example 2, except that the molar excess of the metal used is 50-fold. The product is purified by two successive spin-columns on Sephadex G50/80 equilibrated in 0.1 M sodium phosphate buffer pH 7.3.

Example 8

Preparation of a BSA[Bovine Serum Albumin]-DOTA Conjugate

The procedure for the preparation of a DOTA conjugate of bovine serum albumin [BSA] is similar to that described in Example 1, with a change that the reagents DOTA, sodium bicarbonate, N-hydroxysulfosuccinimide and 1-ethyl-(3,3-dimethylamino)propyl carbodiimide are used in 10:30:10:0.75 molar ratios. Further, activated DOTA is used in a 70-fold molar excess with respect to BSA. Purifications, as outlined in Example 1, yield BSA-DOTA conjugate with a DOTA molar substitution of 1.8:1. In a second, similar preparation, a DOTA substitution of 2.2 is obtained.

Example 9

Preparation of a Yttrium Complex of the BSA-DOTA Conjugate

A 50 mM solution of yttrium chloride in 50 mM hydrochloric acid is prepared using anhydrous yttrium chloride (99.999% purity). The BSA-DOTA conjugate from Example 8, with a DOTA molar substitution of 1.8, is used for complexation of yttrium metal. The complexation procedure, involving BSA-DOTA conjugate and buffered yttrium chloride, is carried out as detailed in Example 2, except that the molar excess of the metal used is 20-fold. The product is purified by two successive spin-columns on Sephadex G50/80 equilibrated in 0.1 M sodium phosphate buffer pH 7.3.

Example 10

Preparation of a Gadolinium Complex of a BSA-DOTA Conjugate

A 51 mM solution of gadolinium chloride in 50 mM hydrochloric acid is prepared using anhydrous gadolinium chloride (>99.9% purity). The BSA-DOTA conjugate, with a DOTA molar substitution of 2.2 is used for gadolinium complexation. The complexation procedure, involving BSA-DOTA conjugate and buffered gadolinium chloride, is carried out as detailed in Example 2, except that the molar excess of the metal used is about 20-fold. The product is purified by two successive spin-columns on Sephadex G50/80 equilibrated in 0.1 M sodium phosphate buffer pH 7.3.

B) Generation and Testing of the LG1 Monoclonal Antibody:

Example 11

Immunization Protocols and Hybridoma Production

Five mice are immunized by i.p. injection of 100 µg of the hLL2-DOTA-Y emulsified in complete Freund's adjuvant. At day 14, the animals are boosted i.p. with the same amount of immunogen emulsified in incomplete Freund's adjuvant. Additional boosts are done: the total number of immunizations being 5 for mouse #1, 6 for mouse #2, and 7 for mouse 3, 4 and 5. For mice 4 and 5 the last immunization is carried out intravenously, with hLL2-DOTA-Y, 100 µg in PBS. The animals are bled after 3 immunizations, and antibodies to the immunogen tested in the sera. The animals are sacrificed 4 days (mouse 1,2,3) and 2 days (mouse 4,5) after the last injection and splenocytes fused with the mouse myeloma cell line SP2/0 ($30 \times 10^6$ SP2/0 cells per fusion) by polyethylene glycol 4000. The cells are then suspended into 50 ml of culture media and dispensed onto five 96-well tissue culture treated plates at 100 µl per well. After 4 hours, a solution of hypoxanthine (0.2 mM), aminopterin (0.8 µM), and thymidine (0.032 mM) is added (100 µl) to each well and three days later, the cultures are progressively weaned of aminopterin by removal of 100 µl of culture media, and addition of the same amount of fresh media containing only hypoxanthine (0.4 mM) and thymidine (0.064 mM). After 10 days, culture media alone is used to feed the cultures. Testing of the hybrids is done at day 10 and 15 post fusion.

Example 12

Testing of Sera

Solutions of hLL2-DOTA-Yttrium, and BSA-DOTA-Yttrium (5 µg/ml in carbonate buffer pH 8.5) are added to ELISA plates for 18 hours at 4° C. The sera of the mice are diluted, and incubated on the plates. A second antibody, peroxidase-conjugated goat anti-mouse IgG (Fc) specific is added, and the binding revealed with a solution of (ortho) phenylenediamine (OPD) and hydrogen peroxide. Seven weeks after the first immunization, antibodies to hLL2 and to DOTA-Y are detected in the sera of the 5 mice (dilution $1\times10^4$ to $1\times10^5$).

Example 13

Testing of the Clones

Culture media supernatant of aminopterin-resistant hybrids are screened by ELISA for antibodies to DOTA-Yttrium using the same assay as used for the sera. The hybrids culture supernatants are tested undiluted on plates coated with BSA-DOTA-Yttrium, and positive hybrids are checked for absence of binding to hLL2, in a similar ELISA assay using plates coated with hLL2. Hybrids found to secrete in their culture supernatants an IgG binding to BSA-DOTA-Yttrium but not to hLL2 are selected for cloning. The following results are obtained:

|  | Total number of hybrids tested | Number of hybrids with IgG Specific binding to DOTA-Y |
| --- | --- | --- |
| Mouse #1 | 220 | Zero |
| Mouse #2 | 268 | Two. |
| Mouse #3 | 249 | Two |
| Mouse #4 | 305 | Sixteen |
| Mouse #5 | 251 | Four |

Example 14

Cloning Procedures

Cells from the above positive hybrids are re-suspended in 200 µl of culture media, and an aliquot of 20 µl is further diluted to 5 ml of the same media. From that stock 12 serial dilutions are done and dispensed on 96-well tissue culture treated plates. After 10 days the clones are tested for IgG binding to BSA-DOTA-Yttrium. From mice #2, 3 and 5, all clones are found negative, while from mouse #4 hybrid termed "4-1-C11" showed all clones positive, while all others were negative. Three positive clones from 4-1-C11 are selected and re-cloned by the same procedure. Testing of the second cloning reveals that all the isolated sub-clones generate an IgG with identical strong positive binding to BSA-DOTA-Yttrium. One of these sub-clones, termed "4-1-C11-G10" is re-cloned. The third cloning generates clones all identically positive. Cells from "4-1-C11-G10-G10" are selected, and that clone is named "LG1".

Example 15

LG1 Sequence Analysis

Both heavy and light chain genes of murine LG1 were obtained by screening a cDNA library constructed from the mRNA that was extracted from LG1 hybridoma cells by using Micro-FastTrack mRNA isolation kit (Invitrogen, Carlsbad, Calif.). The cDNA library had a total of about $3\times10^6$ primary clones and was generated by using Superscript Plasmid System for cDNA Synthesis and Cloning (LiftTechnologies, Rockville, Md.) and following the supplier's specifications.

General molecular cloning methodologies as described by Sambrook et al. (Molecular Cloning: A Laboratory Manual, 2nd Ed., Cold Spring Harbor Press, 1989) were employed for the cDNA library screening and cloning. To screen for the LG1 heavy chain cDNA, a DNA fragment of mouse γ1 chain CH1 region was isolated by AvaII/EcoRI digestion and used as the probe ($C_H$). Similarly, a DNA fragment of mouse λ1 chain constant region isolated by XbaI/XhoI digestion was used as the probe ($C_L$) for the LG1 light chain cDNA screening. The labeling of DNA probes and detection of LG1 heavy and light chain cDNA clones were carried out by using DIG High Prime DNA Labeling and Detection Starter Kit II (Roche Diagnostics, Mannheim, Germany) according to manufacturer's protocols.

Positive clones isolated from the cDNA library were subjected to automated DNA sequencing using the ABI Prism Big Dye Terminator sequencing chemistry and ABI Prism 377 DNA sequencer. 12 of 20 clones selected by the $C_H$ probe encoded same mouse heavy chain cDNA species in different lengths, which included the coding sequences for the secretion signal peptide, VH and full γ2b, as well as 5'- and 3'-noncoding sequences. All 12 clones contained the identical VH sequence, which was assigned as LG1VH. Similarly, 4 of 12 clones selected by the $C_L$ probe encoded a mouse λ chain cDNA composed of the coding sequences for the secretion signal peptide, Vλ and Cλ, and 5'- and 3'-noncoding sequences. The full length Vλ sequences found in three of the clones were all identical and assigned as LG1Vλ.

The amino acid sequences of LG1VH and Vλ were deduced from the respective DNA sequences. The predicted LG1VH and Vλ are composed of 119 and 108 amino acid residues, respectively. Comparison of the LG1VH sequence with the Kabat database (Sequences of Proteins of Immunological Interest, 5th Ed., U.S. Department of Health and Human Services, Washington, D.C., 1991) suggested that it belongs to mouse IgG heavy chain subgroup III(D).

The authenticity of the cloned LG1VH and Vλ was addressed by protein sequencing of LG1. Purified LG1 protein was subjected to 20 cycles of N-terminal protein sequencing analysis by automated Edman degradation. As expected for the existence of both heavy and light chains in an IgG molecule, there were two residues detected in virtually every cycle. However; in each cycle one residue was dominant and the sequence (EVMLVESGGGLVK-PGGSLTL) (SEQ ID NO: 10) matched well with the sequence deduced from the DNA sequenceof LG1VH. The N-terminal of LG1 light chain was probably blocked; resulting in much weaker sequencing signals. Nevertheless, a probable N-terminal light chain sequence, VVTQE[S]ALT[T][S]P[*]E[T]V[T]LY[*] (SEQ ID NO: 11) ([ ] (indicates ambiguous residue; * indicate undetermined residue), resulted from the analysis was consistent with that predicted from LG1Vλ.

Example 16

LG1 Antibody Production

LG1 cells are expanded and adapted to grow in H-SFM media in serum-free conditions. The antibody LG1 is isolated from the culture media by affinity chromatography on Protein G Sepharose with a yield of ~50 mg of IgG per liter of culture media. The purified antibody is analyzed by SDS polyacrylamide electrophoresis, isoelectric focusing, and its isotype is determined by ELISA with a commercially available kit (Southern Biotechnology, Birmingham, Ala.).

LG1 is shown to be an IgG2b, with a lambda light chain, and has a PI of 5.85-6.85.

Example 17

LG1 Binding Studies

LG1 is tested by ELISA for binding to hLL2 and a panel of different metal complexes of DOTA-hLL2. The capture proteins are diluted to 10 µg/ml, and dilutions of LG1 are assayed. Binding is shown using a peroxidase-conjugated goat anti-mouse IgG Fc specific antibody. Identical binding to all the hLL2 DOTA metal complexes is found, while no binding to hLL2 is detected (FIG. 1).

Example 18

Inhibition Studies

Figure 2:
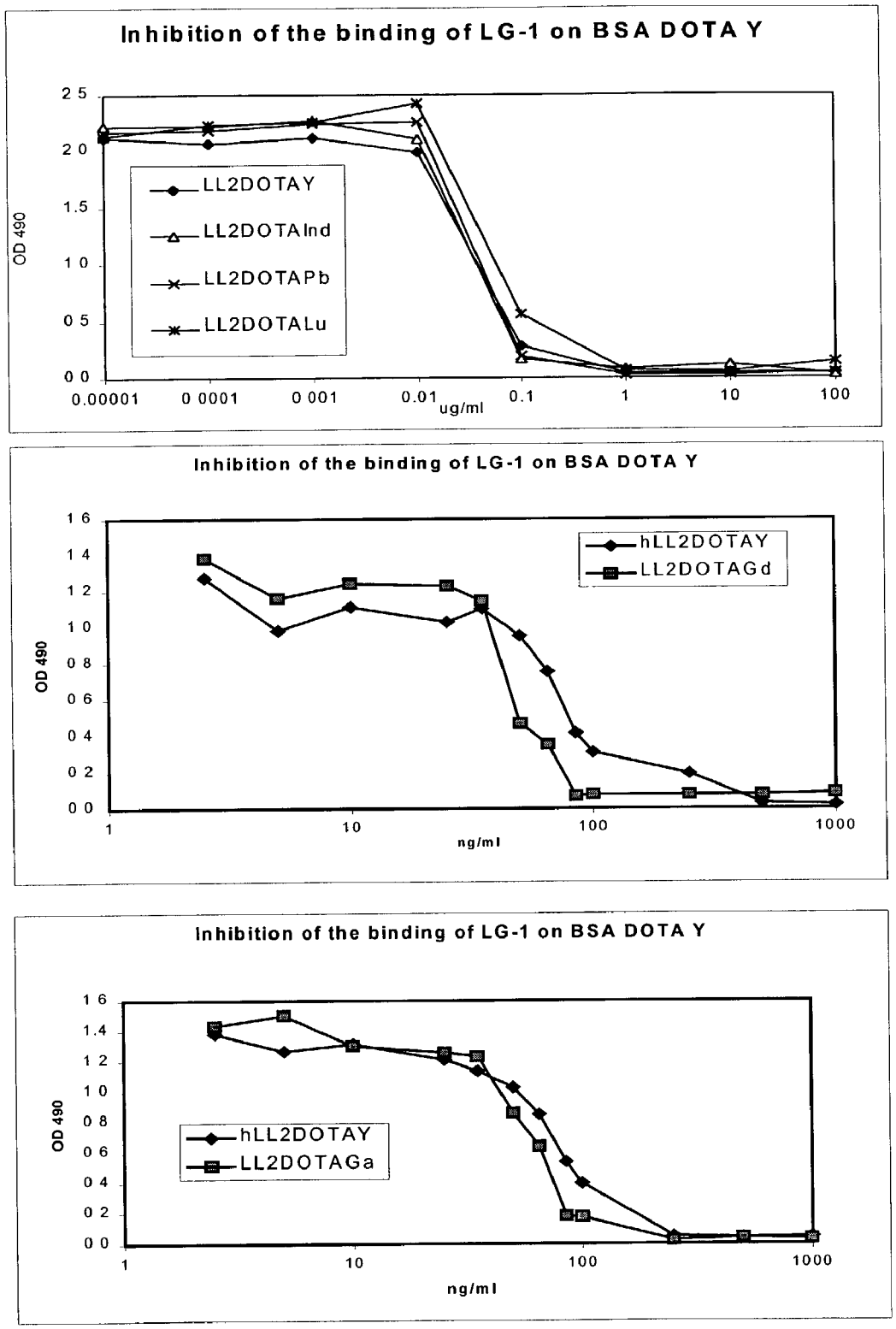
FIG. 2 depicts the inhibition of the binding of LG1 to BSA-DOTA-yttrium by various added metal complexes. Top: yttrium-, indium-, lead- and lutetium-DOTA-hLL2 complexes; middle: yttrium- and gadolinium-DOTA-hLL2 complexes; bottom: yttrium- and gallium-DOTA-hLL2 complexes.

The binding of LG1 to BSA-DOTA-Yttrium is also tested in the presence of a panel of hLL2-DOTA metal complexes by incubating LG1 at concentration 0.1 µg/ml with hLL2 and the DOTA-hLL2 conjugates, at concentration 10 to 0.0001 µg/ml, and then adding to ELISA plates coated with BSA-DOTA-Yttrium. The residual binding of LG1 is revealed as described above, with the peroxidase-conjugated goat anti-mouse IgG Fc specific antibody (FIG. 2). These assays demonstrate that the LG1 antibody is anti-DOTA specific, independent of the metal being bound in the chelate ring.

Example 19

Further Binding Studies

Qualitative binding of the LG1 mAb and derivatives is demonstrated on size-exclusion HPLC by analyzing components in question and then re-analyzing after mixing the first component with its complementary binding pair. In this manner, positive binding of LG1 is shown with hLL2-DOTA, hLL2-DOTA-yttrium, hMN-14-DOTA-yttrium-90, and biotin-D-Phe-D-Lys(DOTA-indium-111), while no binding is observed with hLL2 itself or with indium-111-DOTA-Phe-Lys(HSG)-D-Tyr-Lys(HSG)-NH$_2$ (the indium-111-DOTA complex of a peptide wherein the complex is attached to an alpha-amino rather than an epsilon-amino lysine group). For the Fab fragment of LG1, positive binding to hLL2-DOTA, hLL2-DOTA-yttrium and hMN-14-DOTA-yttrium-90 is shown on SE-HPLC. The msAb, LG1×hMN-14 (Fab'×Fab) is shown by the same analysis to bind to hLL2-DOTA-yttrium.

C) Synthesis and Radiolabeling of DOTA-Peptide Conjugates Recognized by the LG1 mAb:

Example 20

Synthesis of a Di-DOTA-Peptide Bivalent Hapten

Di-DOTA containing peptides are synthesized according to the following exemplary general procedure. Peptides are synthesized on Sieber Amide resin using standard Fmoc based solid phase peptide synthesis to assemble the peptide backbone. An exemplary di-DOTA peptide termed IMP 236 [Ac-Phe-Lys(DOTA)-Tyr-Lys(DOTA)-NH$_2$] (SEQ ID NO: 5) is prepared with the following protected amino acids, added in order to the resin: Fmoc-Lys(Aloc)-OH, Fmoc-Tyr(But)-OH, Fmoc-Lys(Aloc)-OH, Fmoc-Phe-OH, Ac$_2$O. The side lysine side chains are deprotected with tetrakistriphenylPhOSPhifle palladium (O), Pd[P(Ph)$_3$]$_4$. The DOTA ligands are then appended, using a triply protected tri-t-butyl ester derivative of DOTA [one remaining free acid group for reaction] using diisopropylcarbodiimide/O-benzotriazole-N,N,N',N'-tetramethyl-uronium-hexafluoro-phosphate, (DIC/HBTU) and a double coupling procedure. The peptide is cleaved from the resin and the protecting groups removed by treatment with trifluoroacetic acid (TFA). The peptide is purified by reverse-phase HPLC. The reaction sequence yields 0.1064 g of desired peptide from 0.543 g of Ac-Phe-Lys-Tyr(But)-Lys-NH-Sieber amide resin (SEQ ID NO: 12). The identity of the peptide is confirmed by mass spectral analysis, MH$^+$1399.

Example 21

Preparation of a Kit for Radiolabeling the Peptide of Example 19 with Yttrium-90, Indium-111 or other Radiometals The IMP 236 peptide from example 11 is dissolved in 0.25 M NH$_4$OAc/10% HPCD buffer at concentrations of 9, 18, 35, 70 and 140 ug/mL. The solutions are sterile-filtered through a 0.22 um Millex GV filter in one mL aliquots into acid washed lyophilization vials. The filled vials were frozen immediately on dry ice after filling and lyophilized. When the lyophilization cycle was complete the vials were septum-sealed under vacuum and crimp-sealed upon removal from the lyophilizer.

Example 22

Radiolabeling of the above Peptide from Example 19 with Yttrium-90

Yttrium-90 (~400 uCi per kit) is diluted to 1 mL in deionized water and added in one portion to the lyophilized IMP 236 kits of example 12. The kits are heated in a boiling water-bath for 15 min, and the vials then cooled to room temperature. The Y-90 radiolabeled peptides are analyzed by reverse-phase HPLC. HPLC conditions: Waters Nova-Pak C-18, 8×100 mm RCM column eluted at 3 mL/min with a linear gradient from 100% (0.1% TFA in H$_2$O) to 100% (90% CH$_3$CN, 0.1% TFA, 10% H$_2$O). The HPLC analysis reveals that the minimum concentration of peptide needed for complete labeling, with this formulation, is 18 ug/mL. The reverse-phase HPLC trace shows a broad peptide peak corresponding to Y-90-labeled IMP 236. The labeled peptide is seen to be completely bound by LG1 IgG antibody, when mixed with excess of the latter, as analyzed by retention time shift of the Y-90-radiolabeled di-DOTA peptide from low MW to higher molecular weight on size-exclusion HPLC.

Example 23

Radiolabeling of the Above Peptide from Example 19 with Indium-111

Indium-111 [In-111] radionuclide (~300 uCi added per kit) is diluted to 0.5 mL in deionized water and added to the lyophilized kits. The kits are heated in a boiling water bath for 15 min, the vials then cooled. Then, 0.5 mL of 2.56×10$^{-5}$ M cold indium in 0.5 M acetate buffer is added and the kits are again heated in the boiling water bath for 15 minutes. The labeled peptide vials are cooled to room temperature and evaluated by reverse-phase HPLC. HPLC conditions: Waters Nova-Pak C-18, 8×100 mm RCM column eluted at 3 mL/min with a linear gradient from 100% (0.1% TFA in H$_2$O) to 100% (90% CH$_3$CN, 0.1% TFA, 10% H$_2$O). The HPLC analysis reveals that the minimum concentration of peptide needed for good labeling (>95%), with this formulation, is 18 g/mL. The reverse phase HPLC trace shows a broad In-111 labeled IMP 236 peptide peak with one primary and one minor peak. The labeled peptide is seen to be completely bound by LG1 IgG antibody, when mixed with excess of the latter, as analyzed by retention time shift of the In-111-radiolabeled di-DOTA peptide from low MW to higher molecular weight on size- exclusion HPLC.

D) Preparation of a msAb Comprising an anti-DOTA Binding Arm:

Example 24

Preparation of LG1 IgG and an LG1 Fab Fragment

LG1 IgG (a mouse IgG2b) is purified from cell culture supernatant by Protein A chromatography. The bound IgG is eluted from the Protein A column with a pH 3.5 buffer, neutralized, and dialyzed into PBS for storage at 2-8° C. LG1, like other known murine IgG$_2$b antibodies, does not yield a F(ab')2 upon digesting the IgG with pepsin. Instead, LG1 IgG is digested with ficin at neutral pH in the presence of 1 mM cysteine to yield a Fab fragment. The pure LG1-Fab is purified by Protein A followed by Q-Sepharose chromatography.

Example 25

Preparation of hMN14-Fab'×LG1-Fab Multi-Specific Antibody

The hMN14 Fab'-SH fragment is prepared by reducing the F(ab')$_2$ with 1 mM dithiothreitol (DTT). The pure Fab' is obtained by diafiltration into pH 5.3 acetate buffer containing 0.5 mM EDTA. LG1-Fab is derivatized with excess sulfo-SMCC to obtain an activated LG1 Fab-maleimide, containing maleimide groups for linking to the free thiol groups group on the hMN14 Fab' fragment. Following removal of excess sulfo-SMCC by diafiltration into pH 5.3 acetate buffer containing 0.5 mM EDTA, LG1 Fab-maleimide is mixed with an approximately equal amount of hMN14 Fab'-SH to produce the multi-specific conjugate. The conjugation reaction is quenched by the addition of cysteine to a final concentration of 1 mM. The desired product, hMN14-Fab'×LG1-Fab msAb, molecular weight 100 kD, is obtained pure using Superdex 200 column chromatography.

E) In Vivo Validation of the Utility of an LG1-Containing msAb:

Example 26

Trace Radiolabeling of Multi-Specific Antibody

The msAb hMN-14×mLG1 [Fab'×Fab'] is trace-radiolabeled with iodine I-125 by the chloramine T method, and its immunoreactivity estimated at >85% by mixture with excess CEA and subsequent application to an analytical SE-HPLC column (Bio Rad G250, equilibrated in 0.2 M phosphate buffer, pH 6.8; Bio Rad, Richmond, Calif.).

Example 27

Radiolabeling of IMP-236 with Indium-111

The di-DOTA-containing peptide termed IMP 236 is labeled with indium-111 by mixing $2.42\times10^{-9}$ moles of IMP 236 with 2.86 mCi of indium-111 in 0.5 M ammonium acetate buffer, pH 5.5. The labeling mixture is mixed thoroughly and incubated in boiling water for 30 minutes. After cooling, a saturating amount ($6.9\times10^{-9}$ moles) of cold indium is added, and the mixture re-heated at 95° C. for 15 minutes. After cooling, centrifugation and dilution with 0.1 M ammonium acetate, pH 6.5, the In-111-IMP-236 is analyzed.

Example 28

Radioanalyses

Instant thin-layer chromatography (ITLC) is performed on silica-backed plastic sheets (Gelman Sciences, Ann Arbor, Mich.), developed in both 10 mM EDTA and water: ethanol: ammonium hydroxide, 5:2:1, shows under 5% of the radioactivity at the origin in both systems. On SE-HPLC with radiomatic detection, the In-111 radiolabeled peptide elutes near 14.8 minutes, and when mixed with an excess of the msAb hMN-14×LG1 and re-applied to SE-HPLC the radioactivity peak is shifted to a retention time of near 10.4 minutes. These tests show the purity of the In-111-IMP-236 and the retained ability of the In-111-labeled peptide to be bound by the LG1-containing msAb.

Example 29

Biodistribution

NcR athymic nude mice are implanted with cells of the human colonic tumor cell line, termed GW-39. When tumors have reached an appropriate size (>100 mm$^3$) agents are injected. The I-125-radioiodinated msAb is given first, and at different later times the In-111-IMP-236 is administered. The latter radiolabeled peptide is also given alone to a control group of animals. Doses given to each animal are $1.5\times10^{-10}$ moles of I-125-hMN-14×mLG1 (8 uCi of I-125 per animal), and $1.5\times10^{-11}$ moles of In-111-IMP-236. At specified times post-injection of the labeled IMP-236 animals are sacrificed and major internal tissues are collected and quantified for both I-125 and In-111 radioactivity. The data is summarized in the Tables below.

Biodistribution of I-125-hMN-14 × LG1 msAb [Fab' × Fab'] followed 24 h later by In-111-IMP-236 at times indicated post-injection of IMP-236. Data in percent injected dose per gram of tissue. Five animals per group ± standard deviation

| Tissue | I-125, 3 h | In-111, 3 h | I-125, 24 h | In-111, 24 h |
|---|---|---|---|---|
| Tumor | 5.6 ± 0.6 | 6.4 ± 1.1 | 3.5 ± 0.5 | 1.3 ± 0.3 |
| Liver | 0.4 ± 0.0 | 0.2 ± 0.0 | 0.1 ± 0.0 | 0.1 ± 0.0 |
| Spleen | 0.6 ± 0.1 | 0.2 ± 0.0 | 0.1 ± 0.0 | 0.1 ± 0.0 |
| Kidney | 0.6 ± 0.0 | 2.5 ± 0.6 | 0.2 ± 0.0 | 1.0 ± 0.2 |
| Lungs | 0.8 ± 0.1 | 0.2 ± 0.0 | 0.2 ± 0.0 | 0.0 ± 0.0 |
| Blood | 1.6 ± 0.1 | 0.4 ± 0.0 | 0.5 ± 0.1 | 0.0 ± 0.0 |
| Stomach | 3.3 ± 1.1 | 0.1 ± 0.2 | 0.2 ± 0.0 | 0.0 ± 0.0 |

Biodistribution of IN-111-IMP-236 at times indicated post-injection, with no prior administration of msAb. Data in percent injected dose per gram of tissue. Five animals per group ± standard deviation

| Tissue | 30 minutes | 3 h | 24 h |
|---|---|---|---|
| Tumor | 1.6 ± 0.3 | 0.1 ± 0.0 | 0.0 ± 0.0 |
| Liver | 0.3 ± 0.1 | 0.2 ± 0.1 | 0.0 ± 0.0 |
| Spleen | 0.3 ± 0.1 | 0.1 ± 0.0 | 0.0 ± 0.0 |
| Kidney | 4.2 ± 0.7 | 2.2 ± 0.2 | 0.0 ± 0.0 |
| Lungs | 0.7 ± 0.2 | 0.1 ± 0.0 | 0.0 ± 0.0 |
| Blood | 1.0 ± 0.3 | 0.0 ± 0.0 | 0.0 ± 0.0 |
| Stomach | 0.2 ± 0.1 | 0.0 ± 0.0 | 0.0 ± 0.0 |

The data shows that the In-111-IMP-236 bivalent hapten shows a similar biodistribution pattern to the previously administered I-125-hMN-14×LG1 msAb in each tissue tested. When the In-111-IMP-236 msAb is given alone only transient uptake, slightly above blood background, is seen in the tumor xenograft, at only 30 minutes post-injection. The In-111-IMP-236 is quickly eliminated via the renal system, if not bound by the msAb at the tumor.

Additional references of interest include the following:
Barbet et al., *J. Nucl. Med.*, 39:1172-1178, 1998.
Bardies et al., *J. Nucl. Med.*, 37:1853-1859, 1996.
Baxter et al., *Cancer Res.*, 52:5838-5844, 1992.
Boden et al., *Bioconjugate Chem.*, 6:373-379, 1995.
Boerman et al., *Cancer Res.*, 59:4400-4405, 1999.
Bosslet et al., *Br. J. Cancer,* 63:681-686, 1991.
Casey et al., *Br. J. Cancer,* 78:1307-1312, 1998.
Chatal et al., *Hybridoma,* 14:125-128, 1995.
DeNardo et al., *Hybridoma,* 18:13-21, 1999.
De Stasio et al., *Cancer Res.,* 61:4272-4277, 2001.
Feng et al., *Hybridoma,* 17:125-132, 1998.
Gautherot et al., *Cancer (suppl.),* 80:2618-2623, 1997.
Goodwin et al., *J. Nucl. Med.,* 29:226-234, 1988.
Goodwin et al., *J. Nucl. Med.,* 33:2006-2013, 1992.
Goodwin et al., *Cancer Res.,* 54:5937-5946, 1994.
Hosono et al., *J. Nucl. Med.,* 39:1608-1613, 1998.
Hosono et al., *J. Nucl. Med.,* 40:1216-1221, 1999.
Janevik-Ivanovska et al., 8:526-533, 1997.
Karacay et al., *Bioconjugate Chem.,* 11:842-854, 2000.
Kraeber-Bodere et al., *Clin. Cancer Res. (suppl.),* 5:3183-3189, 1999.
Kraeber-Bodere et al., *Clin. Cancer Res. (suppl.),* 5:3190-3198, 1999.
Kraeber-Bodere et al., *J. Nucl. Med.,* 40:198-204, 1999.
LeDoussal et al., *J. Nucl. Med.,* 30:1358-1366, 1989.
LeDoussal et al., *Cancer Res.,* 50:3445-3452, 1990.
LeDoussal et al., *J. Nucl. Med.,* 34:1662-1671, 1993.
Meares et al. *Anal. Biochem.* 142:68-78, 1984.
Peltier et al., *J. Nucl. Med.,* 34:1267-1273, 1993.
Rouvier et al., *Horm. Res.,* 47:163-167, 1997.
Stickney et al., *Cancer Res.,* 51:6650-6655, 1991.
Vuillez et al., *J. Nucl. Med.,* 38:507-511, 1997.
Vuillez et al., *Clin. Cancer Res.* (suppl.), 5:3259-3267, 1999.
Zhu et al., *J. Nucl. Med.,* 39:65-76, 1998.

What is claimed is:

1. An isolated antibody antigen binding fragment thereof that binds to 1,4,7,10-tetrazacyclododecane-N,N',N'',N'''-tetraacetic acid (DOTA) ring, or a metal DOTA complex thereof wherein the DOTA is linked to a hapten via a lysine residue to the epsilon position of one of the DOTA carboxyl groups, wherein the antibody or fragment thereof is a murine or chimeric antibody or antibody fragment thereof comprising the amino acid sequences of the LG1 heavy chain variable region (SEQ ID NO:2) and the LG1 light chain variable region (SEQ ID NO:4).

2. The antibody or antigen binding fragment thereof of claim 1, wherein said metal complex comprises a non-radioactive metal.

3. The antibody or antigen binding fragment thereof of claim 1, wherein said metal complex comprises a radionuclide.

4. The antibody or antigen binding fragment thereof of claim 3, wherein said radionuclide is selected from the group consisting of copper-64, copper-67, gallium-67 gallium-68, zirconium-89, indium-111, scandium-47, yttrium-90, samarium-153, terbium-161, holmium-166, lutetium-177, lead-212, bismuth-212, bismuth-213, actinium-225 and actinium-227.

5. A bispecific antibody or antigen binding fragment thereof that binds to a tissue antigen and 1,4,7,10-tetrazacyclododecane-N,N',N'',N'''-tetraacetic acid (DOTA) ring, or a metal-DOTA complex, wherein the DOTA is linked to a hapten via a lysine residue to the epsilon position of one of the DOTA carboxyl groups, and wherein the bispecific antibody or antigen binding fragment thereof comprising the amino acid sequences of the LG1 heavy chain variable region (SEQ ID NO: 2) and the LG1 light chain variable region (SEQ ID NO: 4).

6. A kit comprising the antibody or antigen binding fragment thereof of claim 1 and an agent selected from the group consisting of 1,4,7,10-tetraazacyclododecane-N,N',N'',N'''-tetraacetic acid (DOTA), a metal complex of DOTA, a polypeptide construct comprising DOTA, and a polypeptide comprising a metal complex of DOTA.

* * * * *

UNITED STATES PATENT AND TRADEMARK OFFICE
CERTIFICATE OF CORRECTION

| | | |
|---|---|---|
| PATENT NO. | : 7,230,085 B2 | Page 1 of 1 |
| APPLICATION NO. | : 10/305268 | |
| DATED | : June 12, 2007 | |
| INVENTOR(S) | : Gary L. Griffiths et al. | |

It is certified that error appears in the above-identified patent and that said Letters Patent is hereby corrected as shown below:

(Col. 39, line 38) please insert --or-- between "antibody" and "antigen".

Signed and Sealed this

Fourth Day of September, 2007

JON W. DUDAS
*Director of the United States Patent and Trademark Office*

```
SEQUENCE LISTING

<160> NUMBER OF SEQ ID NOS: 12

<210> SEQ ID NO 1
<211> LENGTH: 357
<212> TYPE: DNA
<213> ORGANISM: Artificial Sequence
<220> FEATURE:
<221> NAME/KEY: CDS
<222> LOCATION: (1)..(357)
<220> FEATURE:
<223> OTHER INFORMATION: Description of Artificial Sequence: Synthetic
      LG1VH DNA sequence

<400> SEQUENCE: 1 gaa gtg atg ctg gtg gag tct ggg ggg ggc tta gtg aaa cct gga ggg        48
Glu Val Met Leu Val Glu Ser Gly Gly Gly Leu Val Lys Pro Gly Gly
 1               5                  10                  15 tcc ctg aca ctc tcc tgt gca gcc tct gga ttc act ttt act gcc cat        96
Ser Leu Thr Leu Ser Cys Ala Ala Ser Gly Phe Thr Phe Thr Ala His
                20                  25                  30 gcc atg tct tgg gtt cgc cag act ccg gag aag agg ctg gag tgg gtc       144
Ala Met Ser Trp Val Arg Gln Thr Pro Glu Lys Arg Leu Glu Trp Val
            35                  40                  45 gca acc att agt ggt ggt ggt act tac acc tac ttt cca gac agt ttt       192
Ala Thr Ile Ser Gly Gly Gly Thr Tyr Thr Tyr Phe Pro Asp Ser Phe
        50                  55                  60 cag ggg cga ttc acc atc tcc agc gac aat gcc aag aac acc ctg tat       240
Gln Gly Arg Phe Thr Ile Ser Ser Asp Asn Ala Lys Asn Thr Leu Tyr
    65                  70                  75                  80 tta caa atg agc agt ctg agg tct gag gac acg tcc atg tat ttc tgt       288
Leu Gln Met Ser Ser Leu Arg Ser Glu Asp Thr Ser Met Tyr Phe Cys
                    85                  90                  95
```

-continued

```
aca aga cat gga gac tat agg tac gcc ttt ggt tac tgg ggc caa ggg        336
Thr Arg His Gly Asp Tyr Arg Tyr Ala Phe Gly Tyr Trp Gly Gln Gly
        100                 105                 110 act ctg gtc act gtc tct gca                                            357
Thr Leu Val Thr Val Ser Ala
        115
```

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      LG1VH amino acid sequence

<400> SEQUENCE: 2

```
Glu Val Met Leu Val Glu Ser Gly Gly Gly Leu Val Lys Pro Gly Gly
 1               5                  10                  15

Ser Leu Thr Leu Ser Cys Ala Ala Ser Gly Phe Thr Phe Thr Ala His
            20                  25                  30

Ala Met Ser Trp Val Arg Gln Thr Pro Glu Lys Arg Leu Glu Trp Val
        35                  40                  45

Ala Thr Ile Ser Gly Gly Gly Thr Tyr Thr Tyr Phe Pro Asp Ser Phe
    50                  55                  60

Gln Gly Arg Phe Thr Ile Ser Ser Asp Asn Ala Lys Asn Thr Leu Tyr
65                  70                  75                  80

Leu Gln Met Ser Ser Leu Arg Ser Glu Asp Thr Ser Met Tyr Phe Cys
                85                  90                  95

Thr Arg His Gly Asp Tyr Arg Tyr Ala Phe Gly Tyr Trp Gly Gln Gly
            100                 105                 110

Thr Leu Val Thr Val Ser Ala
        115
```

<210> SEQ ID NO 3
<211> LENGTH: 324
<212> TYPE: DNA
<213> ORGANISM: Artificial Sequence
<220> FEATURE:
<221> NAME/KEY: CDS
<222> LOCATION: (1)..(324)
<220> FEATURE:
<223> OTHER INFORMATION: Description of Artificial Sequence: Synthetic
      LG1VL DNA sequence

<400> SEQUENCE: 3

```
gtt gtg act cag gaa tct gca ctc acc aca tca cct ggt gaa aca gtc         48
Val Val Thr Gln Glu Ser Ala Leu Thr Thr Ser Pro Gly Glu Thr Val
 1               5                  10                  15 aca ctc act tgt cgc tca agt agt ggg gct gtt aca act aat aat tat         96
Thr Leu Thr Cys Arg Ser Ser Ser Gly Ala Val Thr Thr Asn Asn Tyr
            20                  25                  30 gcc aac tgg gtc caa gaa aaa cca gat cat tta ttc act ggt cta ata        144
Ala Asn Trp Val Gln Glu Lys Pro Asp His Leu Phe Thr Gly Leu Ile
        35                  40                  45 ggt ggt acc aac aac cga gct cca ggt gtt cct gcc aga ttc tca ggc        192
Gly Gly Thr Asn Asn Arg Ala Pro Gly Val Pro Ala Arg Phe Ser Gly
    50                  55                  60 tcc ctg att gga gac aag gct gcc ctc acc atc aca ggg gca cag act        240
Ser Leu Ile Gly Asp Lys Ala Ala Leu Thr Ile Thr Gly Ala Gln Thr
65                  70                  75                  80 gag gat gag gca ata tat ttc tgt gct cta tgg ttc agc gac cac tgg        288
Glu Asp Glu Ala Ile Tyr Phe Cys Ala Leu Trp Phe Ser Asp His Trp
```

```
Glu Asp Glu Ala Ile Tyr Phe Cys Ala Leu Trp Phe Ser Asp His Trp
            85                  90                  95 gtg ttc ggt gga gga acc gaa ctg act gtc cta ggc                      324
Val Phe Gly Gly Gly Thr Glu Leu Thr Val Leu Gly
        100                 105
```

```
<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      LG1VL amino acid sequence

<400> SEQUENCE: 4
```

```
Val Val Thr Gln Glu Ser Ala Leu Thr Thr Ser Pro Gly Glu Thr Val
  1               5                  10                  15

Thr Leu Thr Cys Arg Ser Ser Ser Gly Ala Val Thr Thr Asn Asn Tyr
             20                  25                  30

Ala Asn Trp Val Gln Glu Lys Pro Asp His Leu Phe Thr Gly Leu Ile
         35                  40                  45

Gly Gly Thr Asn Asn Arg Ala Pro Gly Val Pro Ala Arg Phe Ser Gly
     50                  55                  60

Ser Leu Ile Gly Asp Lys Ala Ala Leu Thr Ile Thr Gly Ala Gln Thr
 65                  70                  75                  80

Glu Asp Glu Ala Ile Tyr Phe Cys Ala Leu Trp Phe Ser Asp His Trp
             85                  90                  95

Val Phe Gly Gly Gly Thr Glu Leu Thr Val Leu Gly
         100                 105
```

```
<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 5

Phe Lys Tyr Lys
  1
```

```
<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 6

Lys Tyr Lys Tyr Lys
  1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: C-term amidated

<400> SEQUENCE: 7

Lys Tyr Lys Tyr Lys Tyr Lys
 1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      Gly-Ser linker

<400> SEQUENCE: 8

Gly Gly Gly Gly Ser Gly Gly Gly Gly Ser Gly Gly Gly Gly Ser
 1               5                  10                  15

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      Gly-Ser linker

<400> SEQUENCE: 9

Gly Gly Gly Ser Gly Gly Gly Ser Gly Gly Gly Ser
 1               5                  10

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Val Met Leu Val Glu Ser Gly Gly Gly Leu Val Lys Pro Gly Gly
 1               5                  10                  15

Ser Leu Thr Leu
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (6)
<223> OTHER INFORMATION: Ambiguous residue, preferably a Ser
<220> FEATURE:
<221> NAME/KEY: VARIANT
<222> LOCATION: (10)
<223> OTHER INFORMATION: Ambiguous residue, preferably a Thr
<220> FEATURE:
<221> NAME/KEY: VARIANT
<222> LOCATION: (11)
<223> OTHER INFORMATION: Ambiguous residue, preferably a Ser
<220> FEATURE:
<221> NAME/KEY: VARIANT
<222> LOCATION: (13)
<223> OTHER INFORMATION: Ambiguous undetermined residue
<220> FEATURE:
<221> NAME/KEY: VARIANT
```

-continued

```
<222> LOCATION: (15)
<223> OTHER INFORMATION: Ambiguous residue, preferably a Thr
<220> FEATURE:
<221> NAME/KEY: VARIANT
<222> LOCATION: (17)
<223> OTHER INFORMATION: Ambiguous residue, preferably a Thr
<220> FEATURE:
<221> NAME/KEY: VARIANT
<222> LOCATION: (20)
<223> OTHER INFORMATION: Ambiguous undetermined residue

<400> SEQUENCE: 11

Val Val Thr Gln Glu Ser Ala Leu Thr Thr Ser Pro Xaa Glu Thr Val
 1               5                  10                  15

Thr Leu Thr Xaa
            20

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Tyr(But)
<220> FEATURE:
<223> OTHER INFORMATION: C-term amidated

<400> SEQUENCE: 12

Phe Lys Tyr Lys
 1
```